(12) United States Patent
Dialameh et al.

(10) Patent No.: US 11,348,480 B2
(45) Date of Patent: *May 31, 2022

(54) AUGMENTED REALITY PANORAMA SYSTEMS AND METHODS

(71) Applicant: NANT HOLDINGS IP, LLC, Culver City, CA (US)

(72) Inventors: Orang Dialameh, Santa Monica, CA (US); Douglas Miller, Los Angeles, CA (US); Charles Blanchard, Los Angeles, CA (US); Timothy C. Dorcey, Santa Monica, CA (US); Jeremi M. Sudol, Los Angeles, CA (US)

(73) Assignee: NANT HOLDINGS IP, LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/741,652

(22) Filed: Jan. 13, 2020

(65) Prior Publication Data

US 2020/0152083 A1    May 14, 2020

Related U.S. Application Data

(63) Continuation of application No. 15/353,016, filed on Nov. 16, 2016, now Pat. No. 10,535,279, which is a (Continued)

(51) Int. Cl.
*G09B 21/00* (2006.01)
*G06F 16/583* (2019.01)
(Continued)

(52) U.S. Cl.
CPC .............. *G09B 21/005* (2013.01); *A61F 9/08* (2013.01); *A61H 3/061* (2013.01); *G06F 16/583* (2019.01);
(Continued)

(58) Field of Classification Search
CPC .............. A61F 9/08; A61H 2201/0157; A61H 2201/501; A61H 2201/5048;
(Continued)

(56) References Cited

U.S. PATENT DOCUMENTS

| | | | |
|---|---|---|---|
| 5,493,331 | A | 2/1996 | Takahashi et al. |
| 5,625,765 | A | 4/1997 | Ellenby et al. |

(Continued)

FOREIGN PATENT DOCUMENTS

| | | |
|---|---|---|
| EP | 10127251 | 6/2000 |
| EP | 1246080 | 10/2002 |

(Continued)

OTHER PUBLICATIONS

"Notice of Reasons for Rejection" dated Jan. 28, 2014. Japanese Patent Application No. 2012-555144. 8 Pages (with English translation).

(Continued)

*Primary Examiner* — Md N Haque
(74) *Attorney, Agent, or Firm* — Stetina Brunda Garred and Brucker

(57) ABSTRACT

There is presented a system and method for providing real-time object recognition to a remote user. The system comprises a portable communication device including a camera, at least one client-server host device remote from and accessible by the portable communication device over a network, and a recognition database accessible by the client-server host device or devices. A recognition application residing on the client-server host device or devices is capable of utilizing the recognition database to provide real-time object recognition of visual imagery captured using the portable communication device to the remote user of the portable communication device. In one embodiment, a sighted assistant shares an augmented reality panorama (Continued)

with a visually impaired user of the portable communication device where the panorama is constructed from sensor data from the device.

35 Claims, 6 Drawing Sheets

Related U.S. Application Data continuation of application No. 14/085,541, filed on Nov. 20, 2013, now Pat. No. 9,526,658, which is a continuation of application No. 13/034,326, filed on Feb. 24, 2011, now Pat. No. 8,605,141.

(60) Provisional application No. 61/339,071, filed on Feb. 26, 2010, provisional application No. 61/307,675, filed on Feb. 24, 2010.

(51) Int. Cl.
G06F 16/955 (2019.01)
A61H 3/06 (2006.01)
H04M 1/72481 (2021.01)
G06V 10/10 (2022.01)
G06V 20/10 (2022.01)
G06V 20/20 (2022.01)
A61F 9/08 (2006.01)
G09B 5/12 (2006.01)

(52) U.S. Cl.
CPC ........... *G06F 16/955* (2019.01); *G06V 10/17* (2022.01); *G06V 20/10* (2022.01); *G06V 20/20* (2022.01); *G09B 5/125* (2013.01); *G09B 21/008* (2013.01); *H04M 1/72481* (2021.01); *A61H 2201/0157* (2013.01); *A61H 2201/501* (2013.01); *A61H 2201/5048* (2013.01); *A61H 2201/5092* (2013.01)

(58) Field of Classification Search
CPC ........... A61H 2201/5092; A61H 3/061; G06K 9/00664; G06K 9/00671; G06K 9/22
See application file for complete search history.

(56) References Cited

U.S. PATENT DOCUMENTS

| | | | |
|---|---|---|---|
| 5,682,332 A | 10/1997 | Ellenby et al. | |
| 5,742,521 A | 4/1998 | Ellenby et al. | |
| 5,815,411 A | 9/1998 | Ellenby et al. | |
| 5,982,853 A | 11/1999 | Liebermann | |
| 5,991,827 A | 11/1999 | Ellenby et al. | |
| 6,031,545 A | 2/2000 | Ellenby et al. | |
| 6,037,936 A | 3/2000 | Ellenby et al. | |
| 6,064,398 A | 5/2000 | Ellenby et al. | |
| 6,064,749 A | 5/2000 | Hirota et al. | |
| 6,098,118 A | 8/2000 | Ellenby et al. | |
| 6,173,239 B1 | 1/2001 | Ellenby | |
| 6,278,461 B1 | 8/2001 | Ellenby et al. | |
| 6,307,556 B1 | 10/2001 | Ellenby et al. | |
| 6,396,475 B1 | 5/2002 | Ellenby et al. | |
| 6,414,696 B1 | 7/2002 | Ellenby et al. | |
| 6,522,292 B1 | 2/2003 | Ellenby et al. | |
| 6,535,210 B1 | 3/2003 | Ellenby et al. | |
| 6,690,370 B2 | 2/2004 | Ellenby et al. | |
| 6,804,726 B1 | 10/2004 | Ellenby et al. | |
| 6,945,930 B2 | 9/2005 | Yokota | |
| 6,951,515 B2 | 10/2005 | Ohshima et al. | |
| 7,016,532 B2 | 3/2006 | Boncyk et al. | |
| 7,031,875 B2 | 4/2006 | Ellenby et al. | |
| 7,181,407 B1 | 2/2007 | Kanevksy et al. | |
| 7,206,434 B2 | 4/2007 | Overton et al. | |
| 7,245,273 B2 | 7/2007 | Eberl et al. | |
| 7,301,536 B2 | 11/2007 | Ellenby et al. | |
| 7,317,473 B2 | 1/2008 | Chen et al. | |
| 7,424,218 B2 | 9/2008 | Baudisch et al. | |
| 7,460,884 B2 | 12/2008 | Sinclair et al. | |
| 7,471,301 B2 | 12/2008 | Lefevre | |
| 7,627,142 B2 | 12/2009 | Kurzweil et al. | |
| 7,641,342 B2 | 1/2010 | Eberl et al. | |
| 7,659,915 B2 | 2/2010 | Kurzweil et al. | |
| 7,696,905 B2 | 4/2010 | Ellenby et al. | |
| 7,768,534 B2 | 8/2010 | Pentenrieder et al. | |
| 7,864,991 B2 | 1/2011 | Espenlaub et al. | |
| 7,889,193 B2 | 2/2011 | Platonov et al. | |
| 7,916,138 B2 | 3/2011 | John et al. | |
| 8,902,254 B1 | 12/2014 | Laughlin et al. | |
| 9,501,618 B1 * | 11/2016 | Wurst | G16Z 99/00 |
| 2002/0101568 A1 | 8/2002 | Eberl et al. | |
| 2002/0112249 A1 | 8/2002 | Hendricks et al. | |
| 2002/0163521 A1 | 11/2002 | Ellenby et al. | |
| 2004/0103139 A1 * | 5/2004 | Hubbard | G06Q 30/0239 |
| | | | 709/201 |
| 2004/0174434 A1 | 9/2004 | Walker et al. | |
| 2004/0183918 A1 | 9/2004 | Squilla et al. | |
| 2004/0189675 A1 | 9/2004 | Pretlove et al. | |
| 2004/0203380 A1 | 10/2004 | Hamdi et al. | |
| 2004/0215612 A1 | 10/2004 | Brody | |
| 2005/0009608 A1 | 1/2005 | Robarts et al. | |
| 2005/0024501 A1 | 2/2005 | Ellenby et al. | |
| 2005/0060088 A1 * | 3/2005 | Helal | A61B 5/0062 |
| | | | 701/532 |
| 2005/0179787 A1 | 8/2005 | Webb | |
| 2005/0208457 A1 | 9/2005 | Fink et al. | |
| 2006/0015337 A1 | 1/2006 | Kurzweil et al. | |
| 2006/0024647 A1 | 2/2006 | Chesnais et al. | |
| 2006/0034530 A1 | 2/2006 | Park | |
| 2006/0129308 A1 | 6/2006 | Kates | |
| 2006/0161379 A1 | 7/2006 | Ellenby et al. | |
| 2006/0190812 A1 | 8/2006 | Ellenby et al. | |
| 2006/0223635 A1 | 10/2006 | Rosenberg | |
| 2007/0096908 A1 | 5/2007 | Chu et al. | |
| 2007/0109619 A1 | 5/2007 | Eberl et al. | |
| 2007/0146391 A1 | 6/2007 | Pentenrieder et al. | |
| 2007/0182739 A1 | 8/2007 | Platonov et al. | |
| 2007/0182755 A1 | 8/2007 | Jones et al. | |
| 2007/0211947 A1 | 9/2007 | Tkacik | |
| 2007/0238074 A1 | 10/2007 | Espenlaub et al. | |
| 2008/0024594 A1 * | 1/2008 | Ritchey | H04N 21/4305 |
| | | | 348/36 |
| 2008/0043934 A1 | 2/2008 | Gallick | |
| 2008/0088469 A1 | 4/2008 | Doemens et al. | |
| 2008/0137550 A1 | 6/2008 | Jurca et al. | |
| 2008/0157946 A1 | 7/2008 | Eberl et al. | |
| 2008/0198159 A1 | 8/2008 | Liu et al. | |
| 2008/0198222 A1 * | 8/2008 | Gowda | H04N 7/185 |
| | | | 348/62 |
| 2009/0116695 A1 | 5/2009 | Anchyshkin et al. | |
| 2009/0141947 A1 | 6/2009 | Kyyko et al. | |
| 2009/0141988 A1 | 6/2009 | Kovtun et al. | |
| 2009/0193055 A1 * | 7/2009 | Kuberka | G06F 16/51 |
| 2009/0271160 A1 | 10/2009 | Copenhagen et al. | |
| 2010/0002909 A1 | 1/2010 | Lefevre et al. | |
| 2010/0023878 A1 | 1/2010 | Douris et al. | |
| 2010/0045665 A1 | 2/2010 | Lefevre et al. | |
| 2010/0045700 A1 | 2/2010 | Lefevre et al. | |
| 2010/0045933 A1 | 2/2010 | Eberl et al. | |
| 2010/0060632 A1 | 3/2010 | Lefevre et al. | |
| 2010/0067745 A1 | 3/2010 | Kovtun et al. | |
| 2010/0068680 A1 | 3/2010 | Quintilio | |
| 2010/0104184 A1 | 4/2010 | Bronstein et al. | |
| 2010/0127971 A1 | 5/2010 | Ellenby | |
| 2010/0134601 A1 | 6/2010 | Lefevre et al. | |
| 2010/0145479 A1 | 6/2010 | Griffiths | |
| 2010/0176953 A1 | 7/2010 | Sherwood et al. | |
| 2010/0188638 A1 | 7/2010 | Eberl et al. | |
| 2010/0208057 A1 | 8/2010 | Meier et al. | |
| 2010/0220891 A1 | 9/2010 | Lefevre et al. | |
| 2010/0232727 A1 | 9/2010 | Engedal | |
| 2010/0239121 A1 | 9/2010 | Meier | |
| 2010/0287511 A1 | 11/2010 | Meier et al. | |
| 2010/0289817 A1 | 11/2010 | Meier et al. | |

(56) References Cited

U.S. PATENT DOCUMENTS

| | | |
|---|---|---|
| 2010/0316281 A1 | 12/2010 | Lefevre |
| 2010/0325563 A1 | 12/2010 | Goldthwaite et al. |
| 2011/0001760 A1 | 1/2011 | Meier |
| 2011/0025532 A1 | 2/2011 | Markram |
| 2011/0050909 A1 | 3/2011 | Ellenby et al. |
| 2011/0090343 A1 | 4/2011 | Alt et al. |
| 2011/0121421 A1 | 5/2011 | Charbon et al. |
| 2011/0177845 A1* | 7/2011 | Fasold ............... G09B 29/008 455/566 |
| 2013/0159454 A1 | 6/2013 | Hunter et al. |

FOREIGN PATENT DOCUMENTS

| | | |
|---|---|---|
| EP | 1354260 | 10/2003 |
| EP | 1119798 | 3/2005 |
| EP | 2207113 | 7/2010 |
| JP | 2002098548 | 4/2002 |
| JP | 2003214888 | 7/2003 |
| JP | 2005160064 | 6/2005 |
| JP | 200665517 | 3/2006 |
| JP | 2006209664 | 8/2006 |
| JP | 2007079620 | 3/2007 |
| JP | 2008171410 | 7/2008 |
| JP | 2008226239 | 9/2008 |
| JP | 2010205281 | 9/2010 |
| KR | 20090036183 | 4/2009 |
| WO | 9859493 | 12/1998 |
| WO | 9942946 | 8/1999 |
| WO | 9942947 | 8/1999 |
| WO | 9949668 | 9/1999 |
| WO | 0020929 | 4/2000 |
| WO | 0163487 | 8/2001 |
| WO | 0171282 | 9/2001 |
| WO | 0203091 | 1/2002 |
| WO | 02059716 | 8/2002 |
| WO | 02073818 | 9/2002 |
| WO | 2005108926 | 11/2005 |
| WO | 2009010195 | 1/2009 |
| WO | 2009040093 | 4/2009 |
| WO | 2009040094 | 4/2009 |
| WO | 2009061420 | 5/2009 |
| WO | 2009061434 | 5/2009 |
| WO | 2009063034 | 5/2009 |
| WO | 2009112057 | 9/2009 |
| WO | 2009112586 | 9/2009 |
| WO | 2009118184 | 10/2009 |
| WO | 2009124601 | 10/2009 |
| WO | 2010002284 | 1/2010 |
| WO | 2010033459 | 3/2010 |
| WO | 2010051825 | 5/2010 |
| WO | 2010060440 | 6/2010 |
| WO | 2010091875 | 8/2010 |
| WO | 2010142895 | 12/2010 |
| WO | 2010142896 | 12/2010 |
| WO | 2010142897 | 12/2010 |
| WO | 2011012142 | 2/2011 |
| WO | 2011012158 | 2/2011 |
| WO | 2011012614 | 2/2011 |
| WO | 2011020793 | 2/2011 |
| WO | 2011028720 | 3/2011 |
| WO | 2011045276 | 4/2011 |
| WO | 2011047888 | 4/2011 |
| WO | 2011047924 | 4/2011 |
| WO | 2011053732 | 5/2011 |

OTHER PUBLICATIONS

"Notice to File a Response" dated Jan. 8, 2014. Korean Patent Application No. 10-2012-7024974 20 Pages (with English translation). Korean Intellectual Property Office.

"Text of the First Office Action" dated Jun. 3, 2014. Chinese Patent Application No. 2011800207158. 17 Pages (with English translation).

Authorized Officer Copenheaver, Blaine, R., "International Search Report" dated May 2, 2011. PCT/US2011/026066. 2 Pages.

Authorized Officer Copenheaver, Blaine, R., "Written Opinion of the International Searching Authority" dated May 2, 2011. PCT/US2011/026066. 14 Pages.

Controller C Naveen Andrew, "Examination Report Under Sections 12 & 13 of the Patents Act, 1970 and the Patents Rules, 2003" dispatched Jan. 1, 2018. 7373/DELNP/2012. 6 Pages.

* cited by examiner

AUGMENTED REALITY PANORAMA SYSTEMS AND METHODS

This application is a continuation of U.S. patent application Ser. No. 15/353,016, filed Nov. 16, 2016, now U.S. Pat. No. 10,535,279 issued on Jan. 14, 2020, which is a continuation of U.S. patent application Ser. No. 14/085,541, filed Nov. 20, 2013, now U.S. Pat. No. 9,526,658 issued on Dec. 27, 2016, which is a continuation of U.S. patent application Ser. No. 13/034,326, now U.S. Pat. No. 8,605,141 issued on Dec. 10, 2013, which claims the benefit of priority to U.S. provisional applications having Ser. No. 61/307,675 filed on Feb. 24, 2010, and Ser. No. 61/339,071 filed on Feb. 26, 2010. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is assistive technologies for disable individuals.

BACKGROUND

Whether termed computer vision, machine vision, or the like, systems providing automated object recognition have traditionally been the subject of considerable interest for implementation in industrial and military applications. One of the ongoing challenges encountered by any system providing object recognition is the variability in the images presented by the same object, and even by the same object viewed from the same perspective, as the result of environmental factors such as the changes in light and shading produced by weather patterns, seasonal transitions, and shifting daylight over the course of a single day. In order to address this and other significant technical challenges, most systems providing reliable object recognition utilize one or more complicated algorithms requiring substantial computing resources for their execution. As a result, many conventional approaches to achieving object recognition may provide identification of an object of interest only after a considerable delay, require a costly and sophisticated computing platform for the processing of object images, or may suffer from both disadvantages. Still, some effort has been directed to provide object recognition as discussed in U.S. patent application publication 2005/0208457 to Fink et al. titled "Digital Object Recognition Audio-Assistant for the Visually Impaired", filed Jan. 5, 2005.

Unfortunately in light of the conventional state of the art, object recognition systems could provide particular benefits to individuals suffering from a sensory impairment, such as blind or visually impaired persons, for example. In principle, the sight of a visually impaired individual might be effectively enhanced by the object recognition capability of an electronic assistant type device providing that functionality. However, in order for an electronic device providing object recognition to most fully benefit the visually impaired individual, the device should address at least three criteria. One of those criteria is that it is desirable that the device providing electronic sight enhancement be portable, so that the visually impaired individual can readily transport the device as desired. One of those criteria is that it is desirable that the device provide a flexible and user friendly interface enabling the visually impaired user to activate and control the object recognition functionality of the device. Furthermore, in order to most fully empower the visually impaired individual while also protecting their safety, it is desirable that the device providing object recognition do so reliably, and do so in real-time, thus enabling the visually impaired user to engage features of his or her present environment.

However, as discussed above, the computing resources required by conventional approaches to achieving object recognition are often substantial. That computing power requirement may considerably exceed the resources of a single portable device under even relatively relaxed performance standards. At best portable devices provide minimal support for character recognition as discussed in U.S. Pat. No. 7,627,142 to Kurzweil et al. titled "Gesture Processing with Low Resolution Images with High Resolution Processing for Optical Character Recognition for a Reading Machine", filed Apr. 1, 2005. When the personal safety of the user and the efficacy of the system providing the object recognition functionality demand that identification of objects be highly reliable and be provided in real-time, the required computing resources far outstrip those available from a single portable electronic device.

One possible avenue for aiding visually impaired users includes interacting with a remote assistant. Ideally a remote assistant should be able to interact with the visually impaired user's full environment. Others have put forth effort toward enabling interactions between a visually impaired user and a remote assistant. U.S. Pat. No. 7,864,991 to Espenlaub et al. titled "System and Method for Assisting a Visually Impaired Individual", filed Apr. 6, 2007, discusses visually impaired individual wirelessly sending audiovisual information about a situation to an assistant. The assistant can then reply back with a solution to the situation. Unfortunately, the assistant lacks complete a complete view of the individual's surrounding environment.

Another example includes U.S. patent application publication 2008/0043934 to Gallick titled "Communications Device for Visually Impaired Persons", filed Aug. 4, 2006, which discusses providing a device having surface sensors to the visually impaired person where a remote assistant can observer the person's interaction with the device.

A more advanced effort includes U.S. patent application publication 2008/0198222 to Gowda titled "System and Method for Tele-presence", filed Feb. 4, 2008, which takes the concept of remote assistance a little further. Gowda indicates that a visually impaired subject can be connected with a guide where the guide can use multi-modal information about subject's environment to aid the subject, possibly by directing the subject to an object. Still, the assistant is limited to the view provided by the subject and also lacks the ability to acquire additional data about the environment.

Interestingly, at best, only limited effort has been directed to utilizing augmented reality systems to aid visually impaired individuals. What has yet to be appreciated is a remote assistant can interact with an augmented reality panorama representing a visually impaired person's environment and its objects. The augmented reality panorama can be built based on sensor data collected via the individual's smart phone, or other sources of ambient data. The assistant can interact with objects, or other aspects augmented reality panorama, and send device commands back to the individual's smart phone to assist the individual or gain further informant about the environment.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Thus, there is still a need for remote assistance for visually impaired individuals.

SUMMARY OF THE INVENTION

The inventive subject matter provides apparatus, systems and methods in which a visual impaired person can seek assistance from a sighted assistant. One aspect of the inventive subject matter includes an augmented reality engine comprising a panoramic engine capable of constructing an augmented reality panorama representing a model of a remote environment and its objects. The panorama can be constructed at least partially based on ambient sensor data collected from a remote visually impaired person's smart phone or other mobile sensing device proximate to the visually impaired person. Preferably the ambient sensor data reflects the remote environment of the person, possibly comprising data associated with images, video, audio, acceleration, orientation, location, odometry, or other sensor data. A sighted assistant utilizes a sighted assistant interface to interact with the augmented reality panorama and with its objects to provide assistive feedback to the remote visually impaired person. The assistant interface presents the augmented reality panorama with an integrated current field of view of the remote person's sensing device. The sighted assistant, human or automated shares the experiences of the remote visually impaired person and interacts with objects within the augmented reality panorama causing one or more device commands to be transmitted back to the person's smart phone. The device commands can instruct the smart phone, or other mobile sensing device, to capture additional information relating to corresponding real-world objects. For example, the device commands can provide haptic or audible feedback to the visually impaired person indicating proximity to one or more objects, or can control selection of one or more applicable object recognition algorithms or routines to acquire additional data.

In some embodiments, the augmented reality panorama includes multi-modal panoramic data where objects in the augmented realty include multiple types of sensory data possibly include visual data, haptic data, kinesthetic data, audible data, or other types of sensory data. Objects can also be tagged with metadata that includes non-visible data. Example non-visible data includes haptic metadata tags, audio metadata tags, or other types of tags that can be leveraged by the assistant to aid the visually impaired user. The multi-modal metadata tags or non-visible tags can be transmitted back to the remote visually impaired person's device in the form of device commands. Thus, the visually impaired person can navigate through their own personalized environment based on non-visible feedback.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
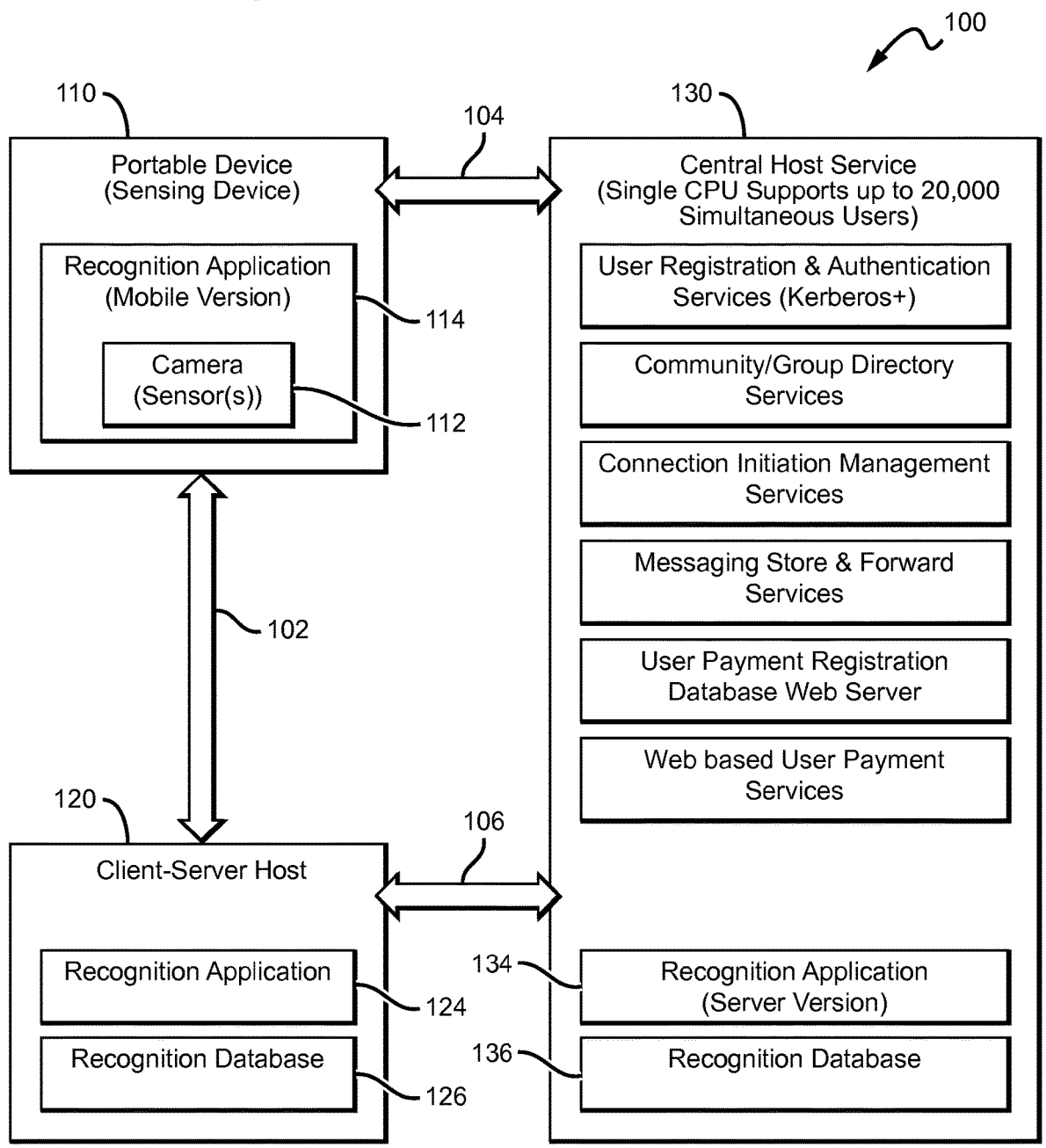
FIG. 1 shows a system for providing real-time object recognition and enhanced sight, according to one embodiment of the present invention.

It should be noted that while the following description is drawn to a computer/server based augmented reality engines, various alternative configurations are also deemed suitable and may employ various computing devices including servers, interfaces, systems, databases, engines, adapters, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclose apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including configuring remote sensing devices to assist a visually impaired person. For example, an augmented reality engine can be utilized by a remote sighted assistant to issue device commands to a remote visually impaired person's smart phone. The commands can instruct the phone to provide guidance for the visually impaired person.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The present application is directed to a system and method providing real-time object recognition and sight enhancement. The following description contains specific information pertaining to the implementation of the present invention. One skilled in the art will recognize that the present invention may be implemented in a manner different from that specifically discussed in the present application. Moreover, some of the specific details of the invention are not discussed in order not to obscure the invention. The specific details not described in the present application are within the knowledge of a person of ordinary skill in the art. The drawings in the present application and their accompanying detailed description are directed to merely exemplary embodiments of the invention. To maintain brevity, other embodiments of the invention, which use the principles of the present invention, are not specifically described in the present application and are not specifically illustrated by the present drawings. It should be borne in mind that, unless noted otherwise, like or corresponding elements among the figures may be indicated by like or corresponding reference numerals.

The present inventors have realized that conventional approaches to providing computer mediated object recognition often result in a less than optimal user experience. Moreover, the present inventors have recognized the acute need in the art for implementation of a nuanced and sophisticated object recognition solution as part of an approach to enhancing sight for the visually impaired. The present application discloses systems and methods directed to providing flexible, powerful, and user responsive solutions configured to accurately and conveniently provide object, facial, context, and environmental recognition as part of an integrated approach to augmenting sight. In one embodiment, for example, a system and method according to the present inventive concepts may enable capturing visual imagery comprising facial features and providing real-time identification of the person having those features. Moreover, in one embodiment, a system and method according to the present inventive concepts may enable capturing visual imagery comprising environmental features and providing real-time identification of a location, as well as perhaps providing navigational information to a remote user according to the location.

Among the many benefits disclosed by the present application are devices, systems, and methods for providing a mobile user with real-time sighted assistance, information, and communication through accessible interfaces. In one embodiment, for example, augmented reality and enhanced sight services can be provided using a camera-enabled portable communication device connected to a user's personal computer (PC) and/or other centralized or distributed computing and communication services.

For example, the systems embodied herein allow a visually impaired user to utilize a camera-enabled portable communication device such as a mobile telephone or personal digital assistant (PDA), for example, to communicate in real-time with either a sighted assistant or an automated computer vision engine which allows them to detect, recognize and track in real-time objects, landmarks, specialized tags, text, signage, or barcodes that may be too distant for low resolution video analysis. Embodiments of the present system offer high resolution image recognition at very high speeds, for example, approximately 5 to 10 frames per second (fps), or more. Such performance is enabled, according to one embodiment of the present invention, by tapping the processing power of the user's PC.

In some embodiments, the results of the object or environmental recognition processing can be enunciated aloud using text-to-speech or pre-recorded tags. That is to say, objects may be identified by providing enunciated speech identification of the object in real-time. Processing and recognition can proceed using identification databases distributed with, or accessible through, embodiments of the present invention. Those databases may include many default entries common to most users, for example. In some embodiments, the identification databases may be open, so that additional layers of information that is personally important to the user can be stored and accessed, either in a storage resource local to the user's PC, or on a central shared community database.

In addition to enunciated speech identification, graphic elements such as hyperlinks, images, two-dimensional (2D) and three-dimensional (3D) graphics, and the like, can be attached and registered to features in a video stream in real-time with low latency and high frame rate. Moreover, the implementation of accessible interfaces using graphics, as well as tactile and speech enabled touch screen interfaces, when combined with speech recognition and gesture recognition, enable use by a broad spectrum of challenged users, such as the visually impaired, elderly, and others with communication or cognitive disabilities.

Specialized tags can be pre-trained in the system allowing a user to simply attach the tags to various objects or landmarks that are not otherwise recognizable by the system. This tagging approach can use features that are recognizable through analysis of video in real-time, such as images identified as optimal for various object recognition algorithms, for example, scale-invariant feature transformation algorithms (SIFTs), speeded up robust feature algorithms (SURFs), or other simpler color or shape based techniques. As the user points the portable communication device camera at one or more objects in one or more scenes, the objects can be automatically analyzed by the system in real-time to identify one or more objects. The system can be further configured to provide linked information or action options regarding the identified object(s) in the display of the portable communication device, either graphically or through audio and tactile interfaces. The links that are generated based on recognition of objects, text, phone numbers, emails, SMS contacts or street signs, for example, as well as those present as prior inputs by the user, can result in more user options for accessing additional information layers, or for initiating communications or location based services.

Embodiments of the present invention implement a hybrid peer-to-peer (P2P) and central processing architecture, thereby enabling use of processing, power and memory resources exceeding the limitations of a camera enabled portable communication device, while avoiding the costs associated with centrally hosted implementations. For example, by transferring layered encoded compressed video and capturing selective regions of interest from within high resolution images for processing on a user PC or a cluster of PCs, video images can receive a depth of analysis otherwise beyond the processing power of the portable communication device alone. In that way, objects, landmarks, text, barcodes, and faces, for example, can be analyzed and identified in real-time.

According to one embodiment of the present invention, remote presence and enhanced vision services allow for remote assistance and training through the display of images or live video captured by the portable communication device to a remote assistant. In addition the remote assistant, linked to the portable communication device through a PC, for example, can take high resolution images using the portable communication device, remotely, based on incoming images. In addition, the remote assistant using the PC can generate panoramas in near real-time by using the distributed processing features and the tiered and layered encoding provided by the system, allowing a progressively higher resolution and alpha blended panorama formed based on registering and auto stitching of incoming images or video frames.

Such panoramas can then be pan tilted and zoomed based on the position of the live incoming video, allowing a mobile user or their remote assistant to obtain a higher resolution view of a scene and to thereby have enhanced sight capabilities, e.g., to see at a greater distance, or to read signage that even those with normal vision could not, or to see in the dark by accessing prior images. Live augmented reality for remote assistance may be enabled where a remote assistant can be in live two-way audio/video communications while having access to the mobile user's real-time position information, for example by means of a geographic information system (GIS).

Personalized training allows a mobile user to train objects into one or more databases of the system, either utilizing the portable communication device, or with the help of a sighted assistant who can perform the training for the user remotely. Community sharing of such databases, as well as access to centrally provided databases, allows for creation of a local database on the portable communication device/PC based system, to enable the real-time performance described above. Embodiments of the system can be configured for universal product code (UPC) bar code detection and recognition, for example, to access additional electronic product catalog information or other user generated information. Embodiments of the system can further associate such information with the image and feature database that the real-time recognition engine and distributed architecture disclosed herein supports. A mobile user can take images of an object of interest through accessible interfaces and then the mobile user or their remote sighted assistant can locate the bar code manually and/or using early vision features, to capture a high resolution photo. The region of interest, e.g., the region including the UPC barcode, can then be transmitted to the PC base station where the bar code is recognized as such, and a UPC database is accessed either locally or over the network.

As mentioned above, the processing resources necessary to support the high frame rate video and fast high resolution photo analysis required for real-time detection, recognition, tracking, as well as utilization of graphic overlay elements (such as hyperlinks), can be obtained efficiently and reliably by connecting a suitably configured camera-enabled portable communication device to the user's or a social networked PC. Such a connection may be provided via an Internet protocol (IP) based overlay network supporting processing by portable communication devices, PCs, or clusters of PCs authorizing such resource sharing, where such distributed architecture is backstopped by a redundant centrally hosted set of services. Local servers enabling device-to-device networks shared by a portable communication device and a mobile internet device (MID) or netbook, for example, can result in a standalone system for the described distributed live video and high resolution image recognition processing.

In one embodiment, an early vision system distributed between the portable communication device and the PC(s) can be used to analyze low resolution video and to recognize objects and scenes as well as areas likely containing information such as text, bar codes, numbers, color, the like. The results of this early vision system, as well as mobile user selections, mobile user location, and time of day, for example, can be used to efficiently control image capture and transfer functions over the IP overlay network. Presumptive regions of interests may then be communicated to the image capture controls in order to identify those regions of the video or lower resolution images already received and analyzed, but requiring high resolution image transfer from the portable communication device. Those high resolution images can then be prioritized for delivery to the PC(s). The decoded images and video can also be directed to back-end recognition and dynamic database generation engines. Dynamically reorganizing databases based on the queues generated above can have a significant impact on recognition performance.

As mentioned above, analysis of real-time video from the portable communication device, and object recognition, can be performed using algorithms such as SIFTS and SURFS while concurrent analysis of the video for text, barcode, or other fine feature regions is performed. Detection of fine features such as text or a barcode can be used to trigger prioritization of high resolution imaging of the region(s) of interest for techniques such as optical character recognition (OCR). In one embodiment, the results of object recognition analysis and analysis of a particular fine feature are combined, so that even a less than optimal OCR analysis can be used to enhance recognition performance.

The present inventors contemplate a wiki type community database where users can submit their personal training databases. Those community databases can be normalized using UPC and electronic product catalog numbers and information, and/or annotated with user generated and reviewed data bases. Database entries may comprise video content, high resolution images or regions of interest, locations, time information, text, and audio, for example. In addition, a database entry may comprise a panorama, as mentioned above and described in greater detail below, which has been tagged, annotated or narrated with pan-tilt-zoom (PTZ) sequences. The inclusion of portable communication devices configured with accessible interfaces in embodiments of the present system enables a mobile user or their sighted remote assistant to download one or more database entries directly to their portable communication device and base station PC dynamically.

Embodiments of the present invention can be implemented for a wide variety of specific uses. For example, healthcare and emergency care interfaces can be enabled through audio enunciated touch screen and speech and gesture recognition interfaces, as well as through compatibility with emergency personal response and remote patient monitoring services. In addition, embodiments of the present invention can be configured to detect 3G or 4G mobile network data quality and to switch between reliable streaming and potentially lossy real-time data transfer. Moreover, embodiments of the present invention can be configured to use multiple network connections such as 3G and/or 4G and beyond, circuit switched Global System for Mobile Communications (GSM), and public switched telephone network (PSTN) standards, through peripherals added to existing PDAs, smart phones, or MIDs, for increased redundancy and reliability in critical applications such as telemedicine and or remote assistance. In some embodiments, use of video content as a view finder, and remote high resolution image capture (e.g., remote cameraman functionality), may be particularly valuable for remote presence functions such as medication intake monitoring and or remote inspection and field repairs. Alternatively, recording audio/video content and location data in a secure fashion can add value when used with multimedia location-based service (LBS) time-card systems used by remote personnel.

FIG. 1 shows system 100 for providing real-time object recognition and enhanced sight, according to one embodiment of the present invention. As shown in FIG. 1, system 100 comprises portable communication device 110, client-server host device 120, and central host server 130. It is noted that the combination of portable communication device 110, client-server host device 120, and central host server 130 is shown for conceptual clarity and is by no means intended to be limiting. For example, in one embodiment, system 100 may comprise portable device 110 and one or more of client-server host device 120 but omit central host server 130, while in another embodiment, system 100 may comprise portable device 110 and central host server 130 but omit client-server host device 120. Further, as known in the art, the operation of each of portable communication device 110, client-server host device 120 and central host server 130 is performed by a microprocessor or a central processing unit (not shown) located in each device or server executing a software stored in a memory (not shown) in each device or server.

As shown in FIG. 1, client-server host device 120 and central host server 130 are remote from portable device 110. Portable device 110, which is equipped with camera 112, is configured to access client server host and/or central host server 130 using respective network communication links 102 and 104. In addition, in embodiments in which client-server host device 120 and central host server 130 are both present, network communication link 106 may mediate communication between those system elements. In various embodiments of the present invention, network communication links 102, 104, and 106 may correspond to communications over the same, or over different networks. For example, network communication link 102 may correspond to communications over a localized network such as Wi-Fi or WiMAX, network communication link 104 may correspond to a wireless mobile carrier network supporting data band communications, and network communication link 106 may correspond to data transfer over a packet network, such as the Internet.

Portable device 110 is shown to include camera 112 and a mobile version of recognition application 114. Portable device 110 may comprise a camera equipped smart phone or personal digital assistant (PDA), for example. Camera 112 may comprise a video camera and/or a still camera, and may be capable of capturing high resolution video and/or still imagery. According to the embodiment of FIG. 1, mobile version of recognition application 114 is capable of running on HTC Windows mobile smart phones, for example, or other suitably configured mobile communication devices. Such devices are offered by substantially all mobile communication providers operating in the U.S. and internationally. Mobile version of recognition application 114 can be configured to provide accessible interfaces which enable a mobile user to connect to a remote assistant for communications and training purposes or to the mobile user's base station client-server host device 120, such as a PC in the home of the mobile user, which typically performs the training and real-time object recognition. Client-server host device 120 can also have accessible interfaces allowing both the mobile user and the remote assistant to easily manage the mobile user's training and database administration needs.

As further shown in FIG. 1, according to the present embodiment, client-server host device 120 includes recognition application 124 and recognition database 126. Although recognition database 126 is shown to reside on client-server host device 120, that need not be the case. Rather, the present inventive concepts can be implemented through variations of system 100 in which a recognition database corresponding to recognition database 126 be merely accessible by client-server host device 120, such as recognition database 136 accessible by client-server host device over network communication link 106, or through recognition database 126 resident on another client-server host device (not shown in FIG. 1) accessible by client-server host device 120 over a P2P network connection (also not shown in FIG. 1). Recognition application 114 residing on client-server host device 120 is configured to utilize either of both of recognition databases 126 and 136 to provide real-time object recognition of visual imagery captured using portable communication device 110 to the remote mobile user of portable communication device 110.

Central host server 130 is shown to include a server version of recognition application 134, recognition database 136, as well as other features. Services provided by central host server 130 are also represented in FIG. 1, and may include a secure means of establishing communication between client-server host device 120 and mobile version of recognition application 114. The P2P transports of the disclosed network architecture eliminate the need for heavy bandwidth hosting, and therefore allow for an economical client-server configuration for users of system 100. Nevertheless, the present inventors contemplate use of central host servers as well, such as central host server 130, for access by users when their own personal base station computers, e.g., the computer(s) running recognition application 124, such as client-server host device 120, are not available.

Central host server version of recognition application 134 can also be configured to operate on client-server host device 120, for example, which enables a substantially self contained configuration in which portable communication device 110 can connect to a netbook or PC running server version of recognition application 134 as well as recognition application 124. This can be accomplished over a P2P Wi-Fi connection between the portable communication device and the PC or netbook. Such a configuration allows users to address mobile carrier data-band coverage issues or for cost savings purposes, but will require the mobile user to carry both systems. In home settings, this can a very practical system configuration.

System 100 also embodies the premise of a personal cloud computing model whereby the mobile user taps the processing power of their own netbook or PC as a remote recognition or training engine. According to the present embodiment, a user can choose their own PC, or that of a family member or friend, as a client-server, while also having access to the centrally hosted options provided by central host server 130, use of which may be associated with some added financial cost to the user. The described configurations result in a flexible system providing high user availability.

Figure 2:
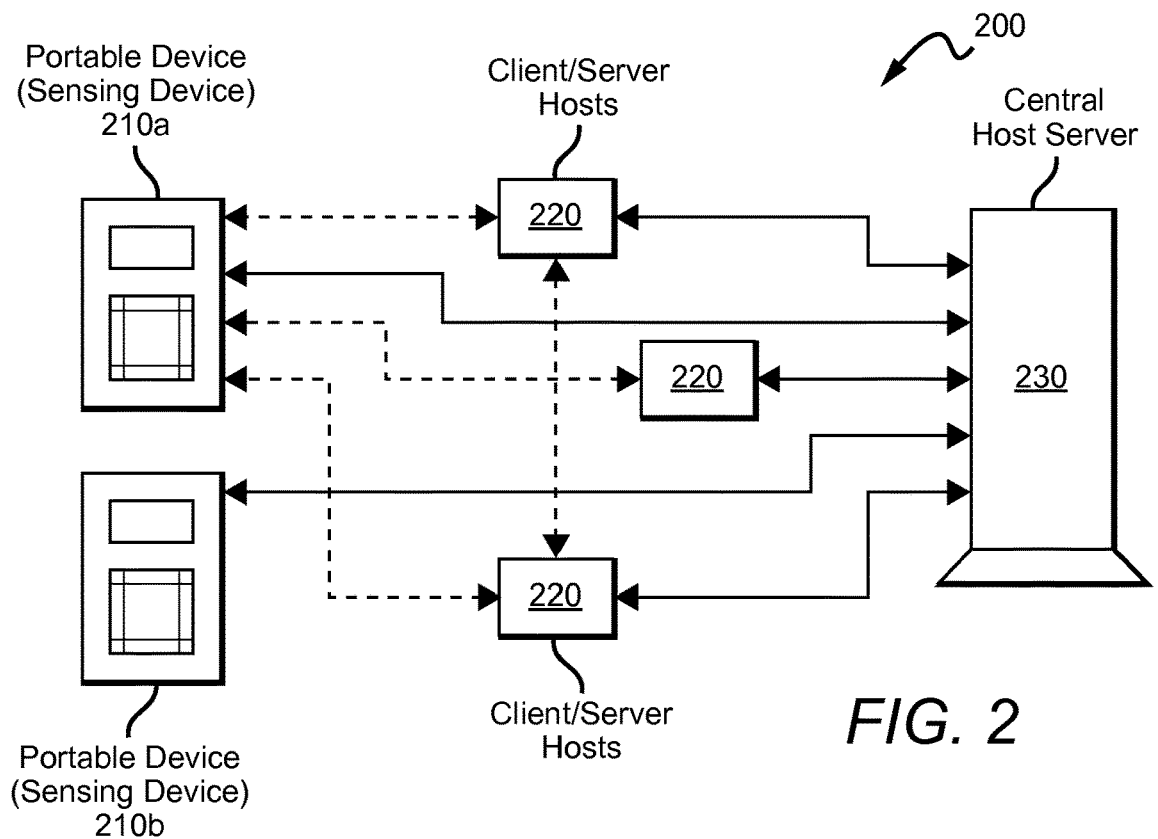
FIG. 2 shows a system for providing real-time object recognition and enhanced sight, according to another embodiment of the present invention.

As shown in FIG. 2, some embodiments of the present invention utilize a hybrid distributed/centralized computing platform, such as the proprietary iVisit™ networking architecture, to enable interaction amongst portable communication device 110, and client-server host device 120 and/or central host server 130, of FIG. 1. FIG. 2 shows system 200 including portable communication devices 210a and 210b communicating with client-server host devices 220 and/or with central host server 230, according to one embodiment of the present invention. It is noted that portable communication devices 210a and 210b, client-server host devices 220, and central host server 230 correspond respectively to portable communication device 110, client-server host device 120, and central host server 130, in FIG. 1.

As shown in FIG. 2, in one instance, a portable communication device, such as portable communication device 210a, may be in communication with a plurality of client-server host devices 220, as well as central host server 230. Alternatively, portable communication device 210*a* may be in communication with the plurality of client-server host devices 220, but be temporarily cut-off from central host server 230. In either of those situations, central host server 230 and/or the plurality of client-server devices 220 are configured to provide a distributed computing platform processing the, for example, visual imagery captured using portable communication device 210*a*. As further shown in FIG. 2, in another instance, a portable communication device, such as portable communication device 210*b*, may be in communication solely with central host server 230. In that situation, central host server 230, running server version of recognition application 134 and utilizing recognition database 136, for example, may be configured to provide a computing platform for processing the visual imagery captured using portable communication device 210*b*.

By way of introduction to the features provided by iVisit, iVisit (www.ivisit.com) is one of the pioneers in the field of IP video conferencing and has operated one of the first Internet IP video conferencing services, with over 2 billion minutes and 4 million downloads to date. Along with commercially available services, iVisit currently hosts over 20 million minutes of multiparty video conferencing per month for free, using its unique P2P network architecture. iVisit has been developing and operating a scalable client-server platform and hosted services over IP networks that work on portable communication devices and PCs. iVisit has registered over 800k users and more than fifty client-server licensees that operate their own services with on-premises server software. Recently completed beta versions of mobile clients configured for use in embodiments of the present invention are supported on Windows portable communication devices demonstrating full duplex video calls (i.e., 160×120 resolution at 14 fps). Such performance has been demonstrated on Windows Mobile PDAs over EV-DO Rev. A under ideal network performance conditions. Moreover, Wi-Fi resolutions of 320×240 can support full screen modes for live video conferencing on PDA phones.

Referring once again to FIG. 1, client-server host device 120 and portable communication device 110 can be configured to provide integrated multiparty audio/video conferencing, presentation, and desktop sharing, Location-Based Services, push-to-talk, messaging, and more. Beta versions of Windows Mobile, iPhone, PC, and Mac configured clients are demonstrating superior performance for live and store & forward communications, while avoiding any adverse impact to wireless networks or devices. Standby times of twenty-four hours and active video calling of more than two hours can be supported on higher performance portable communication devices. Implementation of hybrid central/distributed media transports, adaptive bandwidth management, layered multi-bit rate video and audio encoding also make embodiments of the present invention a promising platform for 3G and 4G application services, and beyond. Simply put, the scalability of the present approach allows the real-time object recognition and sight enhancement functionality disclosed herein to be practical. The present inventors believe that the invention disclosed herein provides the only solution presently able to perform real-time object recognition at frame rates approaching 10 fps over a fixed-mobile platform.

In addition to supporting fixed broadband, embodiments of the present invention support live video over Wi-Fi, WiMAX and any 3G mobile network. Support for WiMax will allow reach into rural and under served areas, as this is the ideal broadband solution showing adoption in rural settings. Asynchronous video messaging can also occur over 1× networks, if reasonably consistent connectivity allowing data rates on the order of 10 kbps is available. The higher bandwidth can be used for either increasing video quality until the processing limits of the portable communication devices are reached, or to support increased numbers of users utilizing the disclosed distributed media transports. Embodiments of the present invention also take into account that a substantial number of users may be on PC clients, and will allow communications between these PC users to be of a higher quality, based on their processing power and ability to support high bandwidth. For example, large and high-definition (HD) video formats may only be enabled on PCs, netbooks, or MIDs having ATOM/SnapDragon, Core Duo, or similar processors.

The audio and video transports suitable for use in embodiments of the present invention can be built on the fast and efficient User Datagram Protocol (UDP). According to embodiments of the present invention, the bandwidth requirements of a client can automatically adjust based on camera, lighting, movement, and video-window size to optimize bandwidth use. The client and host server based services of system 100, for example, can be extended to allow from tens of thousands of concurrent users, to millions of concurrent users, with simple infrastructure expansions. Moreover, communications occurring over embodiments of the present system can be encrypted and made Health Insurance Portability and Accountability Act (HIPPA) compliant. The disclosed embodiments can operate securely over a private LAN, WAN, or VPN. Only authorized users with access to a private domain can communicate with other users on that domain base station server. In some embodiments, authentication is based on Kerberos-like tickets, using Advanced Encryption Standard (AES) encryption.

Multiparty video calls, enabled by embodiments of the present invention, allow for consultations, translation, or interpretation services for the speech and hearing impaired, for example. A simple "add to call" button under a user option menu can allow users to invite additional users to join a call. A "join meeting" function can act similarly to a call-in conference bridge. These P2P video conferencing services can be supported at product launch, either as an additional up-sell to users, or as part of the base package.

Embodiments of the present invention allow a user to "snap and send" high resolution photos during calls or messaging. During these image transfers, video transmission can be affected. However, the "snap and send" functionality enables distribution of very high quality images that can be sent during calls or as audio/video annotated photos during messages and recordings. In addition, some embodiments of the present invention include integrated Global Positioning System (GPS) and mapping services. These options enable communication of the GPS position of a mobile user to authorized groups, contact lists, or particular individuals, for example. Live or recorded GPS positions can be uploaded and displayed on maps, which can, in turn, enable a variety of other Location Based Services. Such connected location based services can be used to enable "Follow Me" or "Friend Finder" type services or for enterprise fleet management and remote workforce management applications, for example.

As discussed above, some embodiments of the present invention include features configured for ease of accessibility by novice, elderly, or sensory impaired users, such as visually impaired remote users, for example. These include the addition of new accessible touch screen interfaces, new accessible portable communication device status indications (such as power, network status, incoming calls or messages).

For elderly and/or novice visually impaired users, contact information for one or more remote sighted assistants can be preprogrammed so that the system can send a message automatically in response to a single button push or other input. For more advanced users, directional keys and accessible touch screen interfaces which enunciate a grid of options in the form of audio menus for the user allow access to all system functions through hierarchical audio menu selections. Recorded human voices can be used for these enunciations with great success and comprehensibility by mobile users in noisy environments.

In some embodiments, keyboard interfaces combined with a suitable text-to-speech engine (e.g., Accapela) can be used to make the system more accessible. Speaker independent name dialing (SIND) and voice commands can also be used to enable speech driven interfaces. Direct connection to compatible TV via Nokia Video Connectivity Cable (CA-75U) or wireless LAN/UpnP, for example, can enable digital magnifier applications.

Recognition application 124 used in some embodiments of the system will allow for considerable control by a remote assistant during the training process. Such control encompasses features such as the remote ability to choose the resolution of the mobile camera during training, the ability to erase features that are detected, the ability to announce range and orientation information on the detected and recognized object, and the ability to quickly enunciate that the previously detected object is no longer in view using a tone, for example. The system is also configured to inform the mobile user regarding light conditions, as well as to allow the remote assistant to control lighting features available on most camera enabled portable communication devices, such as a light-emitting diode (LED) camera flash or a "flashlight" application, for example.

Because remote training of by one or more remote sighted assistants is likely a means of configuring the system for independent use by a visually impaired mobile user of portable communication device 110, synchronizing the training database may be important. A meta-tagging approach allows each database entry to have multiple instance of images, each with a range input for training. As a result, it is possible to extend the range of the system and get more accurate range estimates from objects at various distances than would otherwise be the case. High resolution images can be used for recognizing smaller objects at larger distances. There are now 5 megapixel camera portable communication devices on the market that should allow detection and recognition of objects from longer distances if users can wait for such data to be transmitted. Wi-Fi configurations for in-home use can make this mode more practical.

Figure 3:
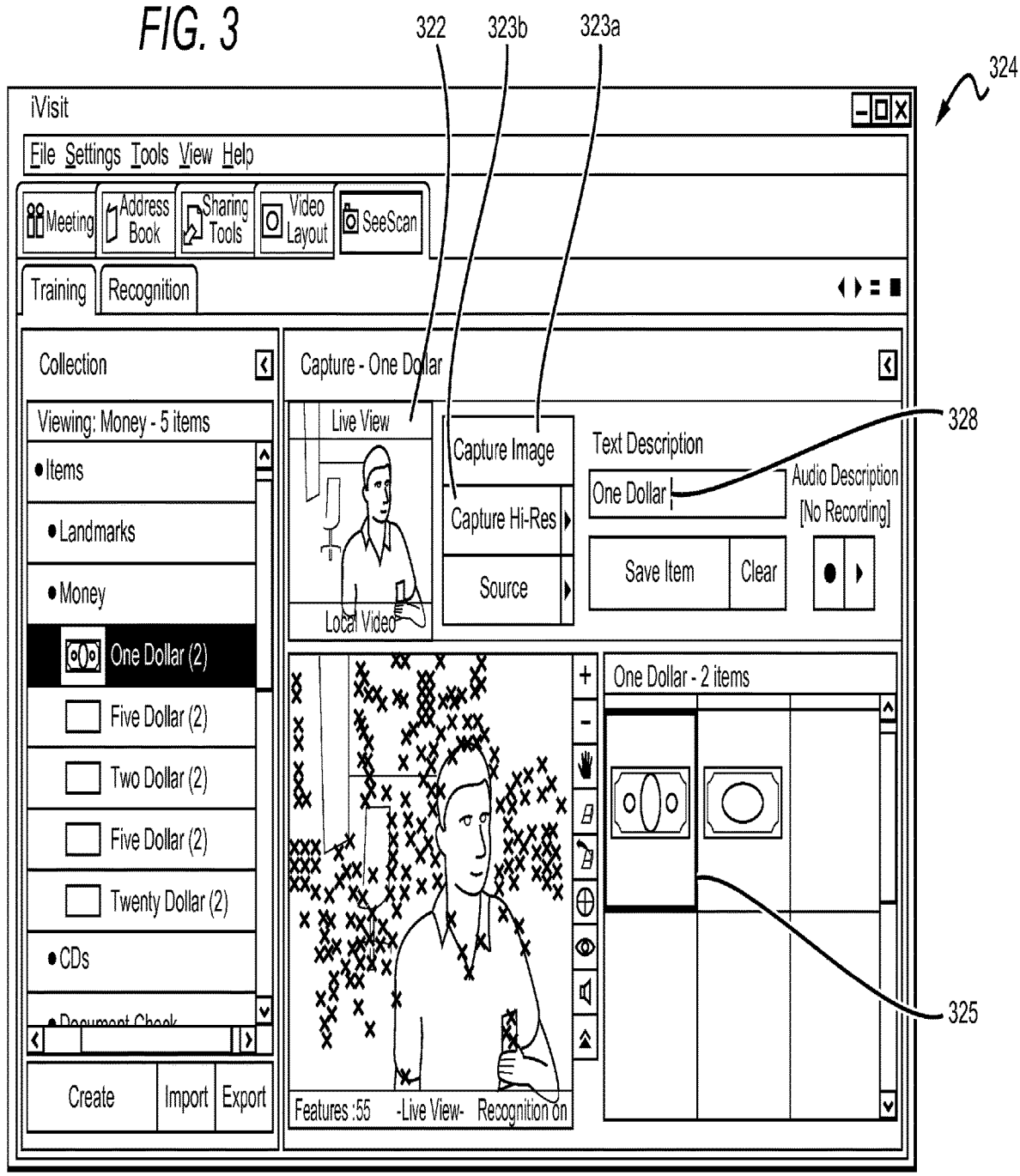
FIG. 3 shows a visual frame on which is captured an example display produced by recognition application 124, in FIG. 1, according to one embodiment of the present invention.

FIG. 3 shows a visual frame on which is captured an example display produced by recognition application 124, in FIG. 1, including an accessible user interface suitable for use by a remote assistant having basic computer skills, according to one embodiment of the present invention. Interface 324 can be considered a sighted assistant interface. Based on a two touch button push a mobile user can connect to a remote assistant with audio and one-way video connection, allowing the remote assistant to act as a remote cameraman to train the system. For example, the remote assistant can first direct the mobile user of portable communication device 110 with audio commands to bring an object of interest into view, using live video from portable communication device 110 in small viewing window 322. Once the object of interest is in full view, the remote assistant can press one of the Capture Image buttons 323a or 323b to either record a frame of video, or request a high resolution image, e.g., captured visual imagery 325. The remote assistant can then enter an object ID in Text Description field 328 that can be used to enunciate the object when the system is in recognition mode.

Some embodiments of the present invention implement object recognition algorithms, such as SIFTS for example, similar to those used in mobile robots to support Navigation localization, mapping, and visual serving. In general, object recognition algorithms perform best when applied to planar, textured objects. The algorithms also reliably recognize three-dimensional objects composed of planar, textured structures, or those composed of slightly curved components. An advantage of object recognition algorithms is that they can provide reliable recognition in realistic environments where lighting conditions, occlusions, and orientation vary dramatically. Three-dimensional deformable objects, however, such as a human face, are typically not handled in a robust manner.

Many object recognition algorithms are capable of achieving high recognition performance in one-to-one verification scenarios and in small databases. Such one-to-one scenarios also more easily allow for multiple images to be used for matching and as a training set, allowing the system to become more robust against variations in lighting and orientation of the object. However, those same algorithms may drop to approximately 80% to 95% recognition rates when trying to identify an object that is subjected to shadowing, when making comparisons to very large databases, and when a database includes very similar objects (e.g., a Diet Coke bottle and a Classic Coke bottle), for example. Several remedies for the described deficiencies are encompassed by the present inventive concepts.

One such remedy includes integration of image processing algorithms, such as fusion of object recognition algorithms with OCR, for example. Distinguishing between Diet Coke and Classic Coke, or recognition of a building or street signage demonstrates objects which may either have very similar patterns to other objects or may not exhibit sufficiently distinctive features for object recognition algorithms alone. Many of the objects that suffer from similarity problems or lack enough distinctive features will include text. Consequently, many of the challenges described above may be addressed using various fusion strategies.

OCR typically requires approximately 3 megapixel images or about 100-200 dpi across the text to be read. The present system can be configured for live video mode to support object recognition, and to automatically switch to a 3 megapixel image capture mode to obtain the required resolution for OCR. The digital zoom of the portable communication device camera can be adjusted based on estimated object recognition based range measurements, for example.

In addition to the use of OCR for reading text on various object labels, UPC bar codes can be used as another means of verification. Bar codes on products can be detected while in live video analysis mode and then the system can switch to a still image mode to capture a higher resolution still image. The high resolution still image can enable reading of the UPC bar code for verification against a UPC database. Moreover, in one-to-one verification scenarios it may be feasible to utilize multiple images for training, thereby enabling object recognition across a range of lighting conditions and/or orientations. For certain stationary structured objects, such as building entrances, for example, it may be possible to capture training images from different orientations at different times of day, representing differing but repeatable lighting conditions that may be encountered. It should also be noted that based on focus group interactions even recognition rates below 90% can be of significant value to visually impaired mobile users.

Human beings have a field of view of approximately 135×200 degrees, but a typical compact camera has a field of view of only approximately 35×50 degrees. Consequently, embodiments of the present invention include features providing automatic panorama generation from live video or higher resolution images can be of substantial value to remote client-server host device users, such as remote assistants. For example, a panorama feature may be used to overcome the tunnel vision problem for remote assistants, as well as to overcome image cropping problems for sign detection and recognition due to camera pointing issues, for visually impaired mobile users.

One solution for generating panoramas uses an auto-stitch technique that presently works by capturing numerous images using an ordinary camera and stitching the individual images together to form a composite image with a much larger field of view, for example, a field of view of up to 360 degrees. The results of auto stitching can be viewed as a computer graphic model that allows the mobile user or remote assistant to look in any direction. Alternatively, the images can be mapped to the surface of a sphere or cylinder to give a 360 degree photograph.

In some embodiments of the present invention, client-server host device recognition application 124 is configured to receive lossless video frames at rates of approximately 5 fps, approximately 8 fps, or approximately 10 fps, for example. Those video frames can be expected to be in proper sequence. As a result, auto-stitch software modules configured to perform image registration can be implemented to process the live image sequences as they are received. At least one auto-stitch implementation allows for discrete scene changes to be recognized as new panoramas. Some versions of client-server host device recognition application 124 included in embodiments of the present invention can be configured to automatically initiate a new panorama when such scene changes have been detected. In addition, the remote assistant can be allowed to navigate back and forth between panoramas manually or based on mobile user position, for example.

SIFT registration of images is less time consuming than multi-band blending. Consequently, in some embodiments, it may prove advantageous to first display unblended results and incomplete panoramas, and then to fill them in as additional images arrive. For example, live video data may be analyzed by the SIFT registration module, providing a graphic overlay that can be displayed over the panorama portion at which the system thinks the portable communication device camera is pointing. Based on remote requests from a sighted assistant, or in response to automatic image parsing of to identify the location of a region of interest, the present system can take higher resolution images of any part of the panorama. A layered encoding may be used to allow additive layers of higher resolution images to be sent for regions of interest, reducing the data transfer profile of the system.

Image analysis algorithms have shown great promise in reliably recognizing location specific features and determining orientation and distance of image based landmarks using SIFT methods. SIFT methods can be used to correlate local invariant features to efficiently match small portions of cluttered images under arbitrary rotations, scaling, changes in brightness and contrast, and other transformations. The image is typically broken into small overlapping sections, each of which is described in a manner invariant to the possible transformations. Then, each section can be individually matched, and the matching pieces reassembled. The described processing sequence can be performed in less than one second, even when matching an image to a large database.

SIFT algorithms can also be applied to the problem of global localization of a mobile user in an indoor setting. For example, SIFT landmarks may be captured in a database over time, resulting in generation of a 3D map of the environment allowing the system to use the 3D landmarks for localization. Odometry can be used to reduce the search of the 3D global localization results, but the system is fully capable of finding location based SIFT features alone. With respect to embodiments of the present system, the inventors contemplate that visually impaired mobile users may need to access landmarks along their intended route as a means of verification, or that they may need to identify and locate an end point destination. Those needs can be met using very sparse maps. In addition, through implementation of streamlining techniques such as route restriction, estimation of rough GPS position, or Location Based Services (LBS) obtainable from wireless networks, for example, the search space of a relevant landmark database can be reduced, eliminating the need for an odometer.

Furthermore, a 2D map may be adequate for some visually impaired mobile user applications. For example, landmarks can be tagged with GIS data allowing a 2D map and localization. Alternatively, such landmarks can be uncorrelated to a GIS database but report progress against a 1D representation of the route landmarks and destinations. SIFT landmarks, even if not tagged with GIS data, can provide relative range and orientation information useful for terminal guidance to a house on a block, for example. SIFT features are most robust against noise and occlusions, but there may be landmarks that are particularly susceptible to vagaries in lighting, reflections, or otherwise lack sufficient SIFT features to be unique. In those instances, text signage detection and OCR can be used to augment landmark or scene recognition.

As previously mentioned, text and signage recognition are features of some embodiments of the present invention. For visually impaired mobile users, however, indiscriminate automated text or signage recognition creates a significant risk of information overload. Unlike a sighted user, who can block out irrelevant visual imagery to focus on text or signage consistent with their needs or interests, a visually impaired user is unable to make such initial distinctions. As a result, embodiments of the present system include "on demand" recognition of signage and certain navigational aids and safety features, such as traffic lights and crosswalk activation buttons, for example.

The ability to automatically detect and read "one demand" features in natural settings has traditionally been very difficult, due to substantial variability in environmental conditions, as well as variability in the characteristics of the "on demand" text itself. Embodiments of the present system include "on demand" recognition functionality implemented using a tunable cascade of strong classifiers, and operate in real-time with a video stream, and with very high accuracy on high resolution still images. For example, client-server host device recognition application 124 analyzing 160×120, 320×240 or 640×480 video streams in real-time can extend the possible text region of interest beyond the areas initially detected and then initiate a one megapixel or greater high resolution still capture and transmission, which can be used for OCR or other enhanced detection and recognition algorithms.

In situations in which text regions of interest extend beyond the boundaries of an image the detector should provide directional scanning guidance to the mobile user, allowing another high resolution image to be captured and transmitted to client-server host device recognition application 124 and stitched to the adjacent region image, thereby overcoming the problem of inadvertently cropped images. One aim of such an approach is to enable automated system assistance for a visually impaired mobile user, to help ensure that the appropriate regions of interest are scanned and that no incomplete (e.g., over cropped) text regions are submitted to the OCR engine. To that end, client-server host device recognition application 124 can be configured to determine the orientation of the text sign of interest, and to provide guidance for the mobile user to change their position with respect to the sign or text region.

In addition, client-server host device recognition application 124 can determine the lowest resolution images needed to successfully recognize text regions, distant landmarks, or signs. Such regions of interest can be encoded in a layered manner to allow faster incremental resolution enhancement by the client-server host device based remote assistant, for example. These regions of interest can then be binarized and passed on to a fine ready OCR engine, such as an ABBYY commercial engine for example. The results can be analyzed to make sure they make complete words, or phrases and non-meaningful results can be identified as such and discarded.

It is noted that training and testing data will be required for "on demand" text and signage recognition. That training data may comprise a collected dataset of proxy, simulation video streams and images, as well as exemplary stitched panoramas, and may include manual labeling of the video, images, and/or panoramas for identification of the desired text areas. Training can include active learning for assembly of large training sets, for example, and may utilize additional interfaces to allow PC/netbook client based remote assistants to capture and label data in cooperation with the mobile user.

In one embodiment, implementation can be in C++, optimized for performance. The recognition algorithms implemented in some embodiments of the present invention work on high resolution megapixel images by segmenting them into patches, and analyzing them at various scales. As a result those embodiments are configured to process both live video stream resolutions and higher megapixel resolutions.

The following summarizes some of the features, performance capabilities, and advantages of embodiments of the present inventive system. Embodiments of the system support video transmission rates from camera enabled portable communication device 110 (e.g., smart phone, PDA) to remote client-server host device 120 of 160×120 at 30 fps, 320×240 at 15 fps; and 640×480 at 5 fps. High resolution image transfer to client-server host device 120, via Wi-Fi for example, can be supported at rates corresponding to 1 megapixel transferred in less than approximately 2 seconds, and 5 megapixels in less than approximately 8 seconds, assuming 400 kbps upstream bandwidth on a 3.5G mobile network. Moreover, in automatic panorama creation mode, transfer rates may correspond to 1 megapixel in approximately 36 seconds, and 5 megapixel images in approximately 3 minutes. Near real-time low resolution panorama creation based on live video 1+ megapixel panoramas can be produced in time intervals ranging from as little as approximately 2 seconds to several minutes over 3.5G networks. The transition from live, low resolution panoramas to 1+ megapixel panoramas can be performed progressively, as a background operation, providing the automated sight enhancement system or the client-server host device based remote assistant with access to improved resolution over time.

For automated modes the systems can be configured so that only regions of interest will be extracted and transferred based on a prior SIFT algorithm analysis of live panoramas. For example, embodiments of the present invention can be configured for SIFT analysis against a dataset of hundreds of entries, using a 1.5 GHz Pentium processor, to achieve 160×120 at 20 fps, 320×240 at 10 fps, and 640×480 at 5 fps. For distant objects, higher resolutions are required, which will slow systems performance depending on the range of the landmark. Text and signage detection can be performed based on live video images at detection speeds of approximately 2 to 15 fps, and recognition speeds of approximately 1 to 2 fps. A region of interest command can be sent from the PC/netbook to the portable communication device at a rate of approximately 1 to 15 fps. Pointing commands can be issued in approximately 2 seconds. A 1 megapixel image capture and transmission can be performed in approximately 2 seconds over Wi-Fi, or approximately 36 seconds over a 3.5G network Megapixel region of interest cropping can result in a 5 to 10 fold improvement in data size and transmission speed. OCR can be performed in approximately 1 to 2 seconds, plus the time required to execute text-to-speech enunciation of the sign content.

SIFT features of landmarks and objects that are close can be recognized even at low resolutions, and therefore can be recognized in real-time, assuming the system video transmission and back end image recognition speeds cited above. SIFTs can both recognize a landmark and determine its range and orientation. The training datasets implemented in embodiments of the present invention can be configured to represent landmarks using multiple ranges and orientations. Distant objects, however, can require higher resolution images and can lack compression artifacts. Consequently, those distant objects are typically slow to transmit over 3.5G mobile networks. Successful OCR of text signage will almost always require megapixel image resolutions given the typical distances and text sizes encountered by mobile users. A client-server host device configuration can overcome the mobile network delays by enabling use of a Wi-Fi connection from the portable communication device to client-server host device recognition application 124, but other methods may be used for intelligent multi-resolution video and scene capture, encoding, and transmission, to speed recognition and data transmission over 3.5G mobile networks.

Real-time video at various resolutions can be provided by the portable communication device, as described above. The real-time video can be requested separately by the automated sight enhancement system, by the client-server host device based remote assistant, or by the mobile user or portable communication device 110. Mobile users of portable communication devices, client-server host device (e.g., PC/netbook) based remote assistants, or the sight enhancement system may also be able to initiate panorama creation, which can both display the live video and separately begin to tile in a panorama using the SIFT auto-stitch methods described previously. The position/perspective of the live video can be adjusted so that it remains centered relative to the panorama surrounding it. The auto stitch SIFT matching and registration stage does not typically require significant processing time and, given that the video images can be sequenced when received from the portable communication device, panorama creation can be near real-time on client-server host device 120.

Blending and color correction can take longer and will typically occur in the background. In cases where the mobile user or client-server host device based remote assistant chooses high resolution (e.g., megapixel) panoramas, the system can be configured to show live video panoramas while guiding the mobile user in scanning their surroundings, automatically taking high resolution images of the mobile user's or client-server host device based assistant's choice at selected points during the scan. These high resolution images can be encoded in a pyramid fashion, so that an additive stream can be sent in the background, thereby enabling progressive enhancement of the resolution for the client-server host device based remote assistant. In automated sight enhancement modes, these live videos can be analyzed in real-time on client-server host device 120 remote from the mobile user of portable communication device 110, utilizing recognition database 126/136 and trained detectors for image parsing, and the same low resolution SIFT methods for close landmark recognition, for example. The results of that analysis can be used to determine landmarks that are recognizable at available resolutions in real-time, while the text signage detectors can also prompt users in real-time when a text region of interest is in view. The mobile user can then be prompted by the text detectors to adjust the aim of the portable communication device camera, and the sight enhancement system can take a high resolution image from a perspective determined to be most likely to avoid truncated signs or landmarks.

Various region of interest extension strategies can be used to provide camera aiming cues to the mobile user, based on analysis of the live videos and constructed panoramas. The mobile user can then be trained to hold the portable communication device camera steady for the sight enhancement system to take a megapixel image. These high resolution images can again be encoded in a pyramid fashion so that the additive stream can be sent in the background and be processed to progressively enhance resolution for the OCR recognition backend. In some embodiments, lower resolution detectors can be employed to determine the most likely resolution needed for recognition of an identified region of interest. However, the automated default settings can be overridden according to manual inputs by the mobile user and/or the client-server host device based remote assistant, enabling the users to select a resolution suitable for their choice of viewing distance.

Figure 4:
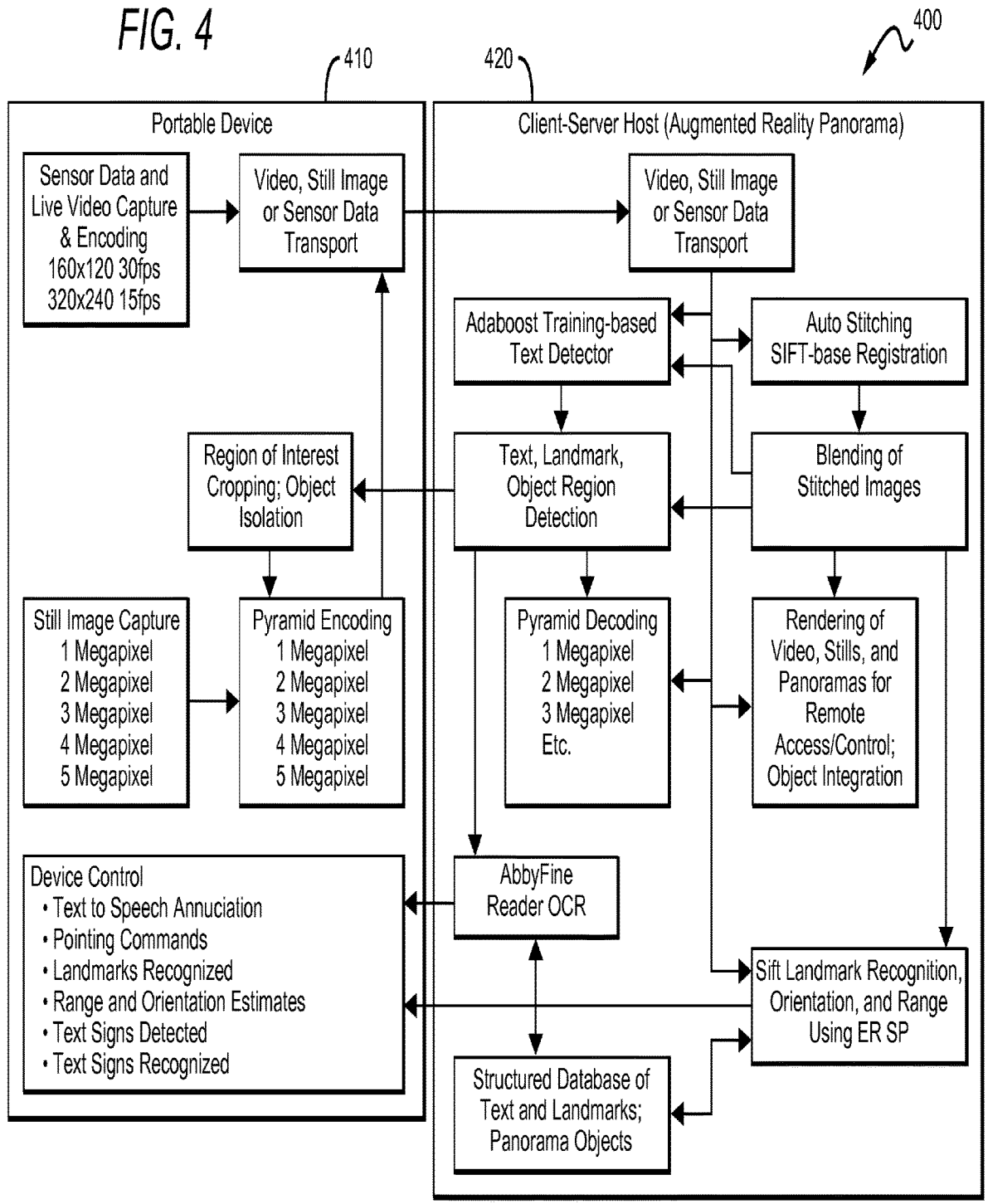
FIG. 4 shows a functional overview of a system for providing real-time object recognition and enhanced sight, according to one embodiment of the present invention.

FIG. 4 shows a functional overview of the described sight enhancement system, according to one embodiment of the present invention. Sight enhancement system 400 includes functionality provided by portable communication device 410, functionality provided by client-server host device 420, and the interrelationship between those system nodes. Referring back to FIG. 1, the functionality provided by portable communication device 410 and client-server host device 420, in FIG. 4, can be seen to correspond respectively to the operation of mobile version of recognition application 114 on portable communication device 110 and recognition application 124 on client-server host device 120, in FIG. 1. The approach outlined above is designed to correspond to human peripheral and central vision, and thus to enable augmentation of those neurophysiological system for the visually impaired. For example, the described low resolution live video analysis can be seen to correspond to the ability of a sighted person to use peripheral vision to make out general shapes and landmarks, whereas the higher acuity of central vision is required to read and recognize text, distant objects, or regions having fine details. In embodiments of the present invention, region of interest detection can be performed using live video or low resolution panoramas before committing resources to more time consuming high resolution recognition.

According to some embodiments of the present invention, spatial and time layered video and still image encoding and decoding can be implemented to enhance the performance of video codecs, such as the H263+ video codec, for example. Pyramid fashion encoded progressive resolution algorithms can be implemented in order to optimally support a heterogeneous mix of broadband and dial-up connections. In a point-to-point setting, for example, the media transmission rate can be continuously adjusted to optimally utilize the capacity available on the point-to-point path. That approach allows the system to deliver an optimal user experience, without having undue impact on other traffic sharing the path. When there are multiple recipients, there is almost certain to be variation in the amount of data that each recipient can receive at any given moment. This may be due to a heterogeneous mix of broadband versus dial-up users in a large group conferencing setting, or may simply be due to network congestion and/or delays. If a sender is to send the same data to all client nodes, then the sender must typically choose between targeting the lowest capacity receiving node, thereby degrading the experience for better equipped receivers, or transmitting at a higher rate with the knowledge that paths to less equipped receivers will likely be overloaded.

To address this problem, embodiments of the present invention are configured to encode video in multiple layers, which can be selectively forwarded to produce different rate data streams, while maintaining the integrity of the decoded video. Such layering can be achieved through modifications to the H.263+ codec that allow different frame rates to be selected from a single stream. The present approach is configured to support data rates varying within an approximately six to one (6:1) ratio (e.g., if video is encoded at 60 kbps, then it can serve recipients at data rates ranging from 10 kbps to 60 kbps). As a result, different recipients can receive video with the same spatial quality, but at different frame rates. Similar encoding schemes can also be implemented to support different spatial layers. Thus, for example, one recipient may receive video at 160×120 resolution, while another receives an additional enhancement layer which allows 320×240 resolution.

Embodiments of the present invention include a new Replication and Forwarding Protocol (RFP), which offers several significant advances in routing capability. Distributed processing and access to PC/netbook client-server resources in circumstances in which concurrent access to a central host server, through the Internet for example, is unavailable or undesirable, requires enablement of self contained clusters where video and images can be transferred between devices, such as on a wireless LAN for example. To accomplish this, a self contained client-server architecture that uses P2P media transports can be used effectively to (1) treat each media source independently, so that data replication might occur at different points in the network for different members of a cluster, and (2) enable cascading of multiple points of data replication to create distribution trees of variable depths.

With the two advances mentioned above, one embodiment of the present system architecture is configured such that each media origination node is co-located with a replication and forwarding node. In effect, each client (e.g., mobile client or PC/netbook client-server) can act as a media distribution server for the media generated at that client. That approach supports a symmetric P2P distribution model in such a way that the point(s) of data replication can be readily moved away from the originating source node whenever such alternative points of replication became available via the distributed routing trees.

In addition to these changes in routing capabilities, embodiments of the system RFP are designed to support the transport level services that may be essential in real world deployment. Those can include hop-by-hop flow control/congestion avoidance to ensure that no downstream node is sent data at a higher rate than it can successfully receive it, for example. Moreover, embodiments of the system RFP include facilities for acknowledgment and retransmission of data that must be delivered reliably, without necessarily requiring retransmission from the originating source node. Hence, embodiments of the present system RFP can be viewed as a hybrid between traditional application level distribution servers and a network level multicast solution. Like IP multicast, the disclosed RFP can allow for the creation of distribution trees with an arbitrary number of replication points. Unlike IP multicast, however, the disclosed RFP can also address key transport level problems which are difficult to solve in a 1-to-arbitrary-N routing context. With the basic transport capabilities now deployed and tested, the present inventors herein disclose three additional embodiments of distribution schemes using RFP nodes located outside the media originating client (e.g., source node).

One such embodiment can be characterized as a "Conference Server" model where a centrally located RFP node with a high-speed network connection provides replication services for all members of a conference cluster in a star topology. A second embodiment can be characterized as a "local proxy/cache" model in which a dedicated RFP node located near a cluster of recipients provides replication services for all media destined toward that cluster. For example, an RFP node located at a campus or on a LAN could provide replication services to all local recipients. A third embodiment takes the form of a dynamic P2P model where end user clients perform replication and forwarding services for other clients receiving the same stream.

Figure 5:
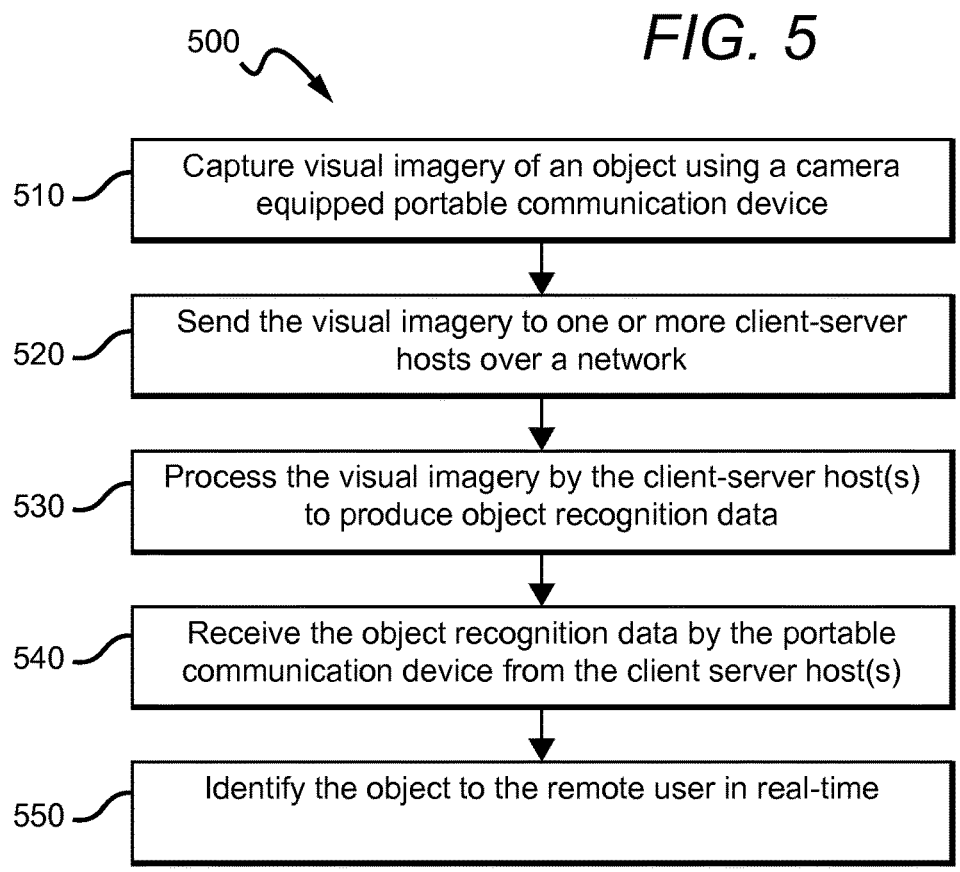
FIG. 5 is a flowchart presenting a method for providing real-time object recognition and enhanced sight, according to one embodiment of the present invention.

FIG. 5 shows flowchart 500 describing the steps, according to one embodiment of the present invention, of a method for providing real-time object recognition and enhanced sight. Certain details and features have been left out of flowchart 500 that are apparent to a person of ordinary skill in the art. For example, a step may comprise one or more substeps or may involve specialized equipment or materials, as known in the art. While steps 510 through 550 indicated in flowchart 500 are sufficient to describe one embodiment of the present method, other embodiments may utilize steps different from those shown in flowchart 500, or may include more, or fewer steps.

Referring to step 510 of flowchart 500 in conjunction with FIG. 1, step 510 comprises capturing visual imagery of an object by a portable communication device including a camera. Step 510 may be performed using portable communication device 110 including camera 112. As a specific example, let us consider portable communication device 110 to be a smart phone comprising a video camera capable of capturing high resolution imagery. In that example, step 510 can correspond to a user of the smart phone shooting video using the high resolution video camera.

The method of flowchart 500 continues with step 520, which comprises sending the visual imagery to at least one client-server host device over a network. Step 520 may be performed by portable communication device 110, using network communication link 102 to send the captured visual imagery to client-server host device 120. In some embodiments, as shown for example by FIG. 2, portable communication device 110 may be linked to a plurality of client-server host devices over a P2P network, for example.

Referring now to step 530, in FIG. 5, step 530 of flowchart 500 comprising processing the visual imagery using a recognition application on the client-server host device to produce object recognition data. In one embodiment, step 530 may be performed by recognition application 124 on client-server host device 120. Moreover, referring to a FIG. 2, in one embodiment, a plurality of client-server host devices 220, each running a recognition application 124 may serve as a distributed computing platform for the processing performed in step 530. Alternatively, in one embodiment, the processing may be performed using server version recognition application 134 by central host server 130. As previously mentioned, the processing of step 530 may be performed using one or more of a SIFT algorithm, a SURF algorithm, and OCR.

Moving on to step 540 of flowchart 500, step 540 comprises receiving the object recognition data from the at least one client-server host device by the portable communication device over the network. As may be seen from FIG. 1, step 540 may correspond to receipt by portable communication device 110 of object recognition data produced by recognition application 124, over network communication link 102.

In step 550 of flowchart 500, the object is identified to the remote user of portable communication device 110 in real-time. Step 550 is performed using portable communication device 110. In one embodiment, portable communication device 110 may include mobile version of recognition application 114, which may include an interface configured to provide enunciated speech identification of the object in real-time, and/or to enable use of the present method by a visually impaired remote user. In one embodiment, the visual imagery comprises environmental features and identifying the object comprises identification of a location. In that latter embodiment, the present method may further comprise providing navigation information to the remote user according to the identified location.

Figure 6:
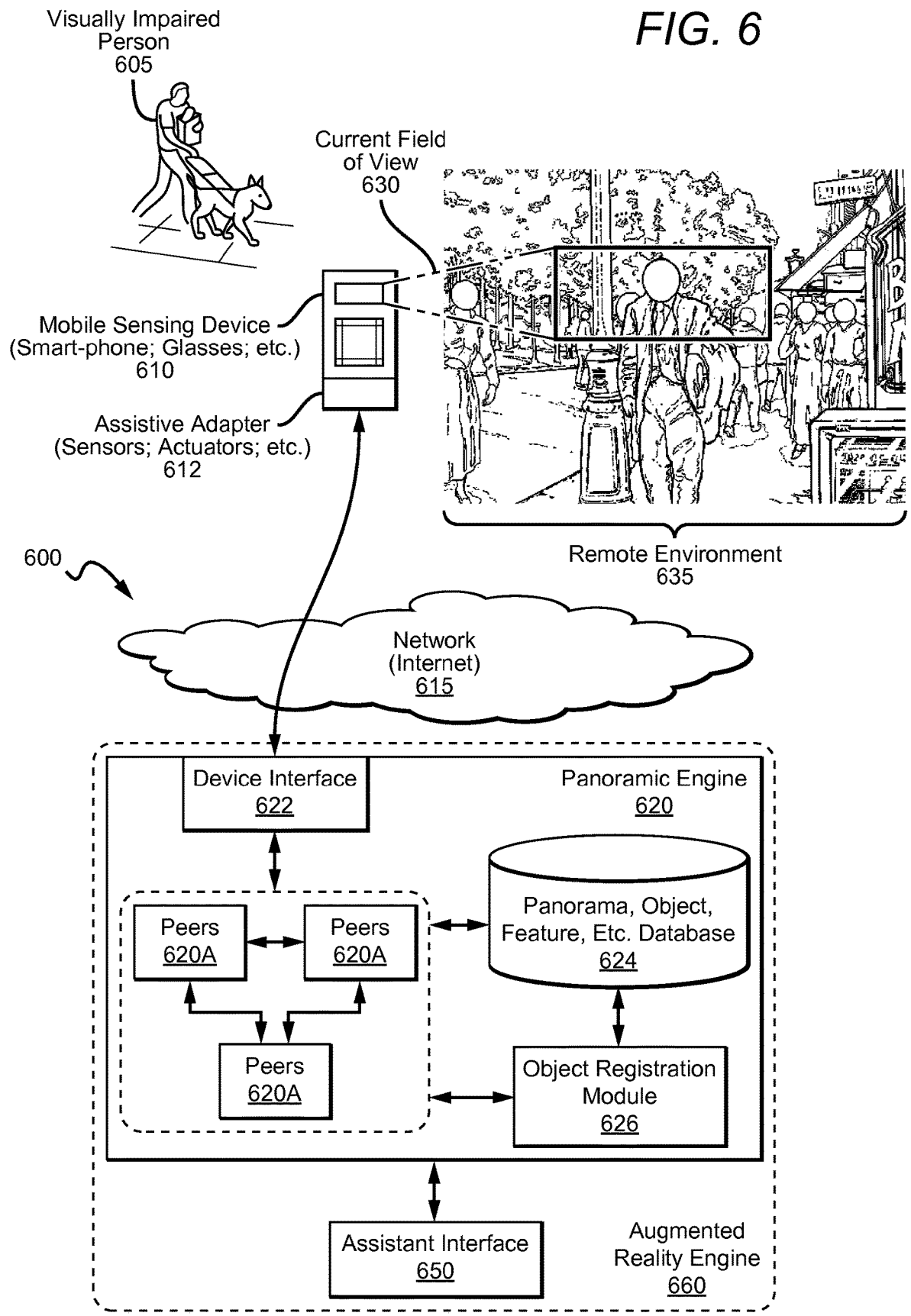
FIG. 6 shows another system capable of providing enhanced sight to a visually impaired person.

In FIG. 6, system 600, similar to the system described in reference to FIG. 1 and FIG. 2, provides enhanced sensing capabilities to visually impaired person 605 through interaction with augmented reality engine 660. Augmented reality engine 660 constructs an augmented reality panorama of remote environment 635, including its objects, which is presented directly to a sighted assistant via assistant interface 650. Rather than having only visually impaired person 605 interacting with the augmented reality panorama, the sighted assistant also interacts directly with the augmented reality panorama to assist visually impaired person 605 as described in the following discussion.

The following discussion is presented from the perspective of a sighted assistant. Therefore, the visually impaired person 605 and remote environment 635 are considered remote relative to the sighted assistant. The term "remote" is used euphemistically to indicate the sighted assistant is physically separated from visually impaired person 605 by a distance sufficient to render physical assistance impracticable, typically more than about 50 meters. For example, visually impaired person 605 could be located on a different continent from assistant interface 650. Thus, a sighted assistant can be geographically separated from visually impaired person 605.

Visually impaired person 605 utilizes mobile sensing device 610 to capture ambient sensor data via one or more sensors. As discussed previously, mobile sensing device 610 can include a smart phone or other types of portable devices. Examples of other portable devices can include glasses, single purpose devices, or other computing devices configured to acquire and send data over network 615. Mobile sensing device 610 includes at least one sensor, preferably a camera, capable of acquiring sensor data. Mobile sensing device 610 can include other types of sensors including accelerometers, microphones, magnetometers, bio-sensors, bar code readers, RFID readers, odometers, GPS, radios, or other types of sensors. In some embodiments, sensors can also include personal area sensor webs of one or more interconnected bio-sensors configured to obtain data regarding physically well being of visually impaired person 605; blood pressure, neural activity, heart rate, temperature, breathing rate, perfusion data, or other health metrics for example. Mobile sensing device 610 obtains data from each of its sensors and prepares the sensor data for transport over network 615 to augmented reality engine 660.

In some embodiments, mobile sensing device 610 can be configured to acquire capabilities beyond its intended purposed via an assistive adapter 612. Assistive adapter 612 couples with mobile sensing device 610 via one or more coupling interfaces, wired or wireless (e.g., Bluetooh or 802.15x, USB, Wireless USB, Firewire, PCIe, Light Peak, RS-232, Zigbee, eSATA, Ethernet, etc.). Adapter 612 can include additional sensors that are not present within mobile sensing device 610. For example, an iPhone™ lacks an RFID reader. Adapter 612 could include an RFID reader configured to couple with the iPhone via a USB connection where the RFID reader can capture wireless RFID data, for example the IDBLUE™ reader (see URL www.idblue.com) could be adapted for use with the disclosed subject matter. In addition, adapter 612 can provide other types of enhanced capabilities possibly including wide band communication (e.g., WiMAX, WiGIG, ad-hoc networking, UWB, WirelessHD, etc.), echo location capabilities, haptic feedback actuators (e.g., vibrators, Braille interface, etc.), enhanced audio outputs/inputs (e.g., stereo, filters, etc.), or other enhanced capabilities.

Mobile sensing device 610, possibly in cooperation with adapter 612 or other external sensors, is preferably configured to acquire ambient sensor data representative of remote environment 635 or, more specifically, current filed of view (FoV) 630. The sensor data can be considered ambient sensor data in view that mobile sensing device 610 can be configured to obtain data from its sensors continuously without directed action from visually impaired person 605. Ambient sensor data can be actively collected or passively collected, even on a sensor-by-sensor basis. Actively collected sensor data is considered to include data collected under command of visually impaired person 605 or under command of the sighted assistant. Passively collected sensor data comprises data simply collected while sensors are active. For example, mobile sensing device 610 could have all sensors in a "collect" mode where mobile sensing device 610 obtains ambient sensor data regardless of circumstances in remote environment 635.

Ambient sensor data representative of remote environment 635 can also be collected by other data sources beyond mobile sensing device 610 or adapter 612. For example, publicly accessible live camera feeds can also be accessed where augmented reality engine 660 integrates such "external" ambient data into construction of an augmented reality panorama. Other data sources within system 600 can include government database (e.g., geographic surveys, etc.), military or private vehicles (e.g., drones, planes, automobiles, etc.), municipality sensors (e.g., police radio, live highway camera feeds, fire stations, etc.), security agencies, satellites, Google® StreetView™, or other sources of ambient sensor data, public or private.

Ambient sensor data is sent to augmented reality engine 660 over network 615 where augmented reality engine 660 can include remote device interface 622, panoramic engine 620, panoramic database 624, or object registration module 626. One should appreciate that network 615 can comprise one or more networking infrastructures, wired or wireless, including the Internet, cell networks, WAN, LAN, VPN, PAN, or other types of networks. Remote device interface 622 can be configured to receive the ambient sensor data from mobile sensing device 610 according to various desired methods. In some embodiments, remote device interface 622 can comprise a web server offering an URL or web services API accessible to mobile sensing device 610. In other embodiments, remote device interface 622 can include a dedicated communication links supporting one or more proprietary protocols. For example, mobile sensing device 610 can have an installed application (e.g., recognition application 114 of FIG. 1) configured to communicate directly with a complementary application operating as remote device interface 622 (e.g., recognition application 124 or 134 of FIG. 1).

One might recall the disclosed infrastructure can operate in a peer-to-peer fashion (see FIG. 2). In a similar vein, panoramic engine 620 can include multiple components coupled with each other over a network. For example, peers 620A can represent one or more separate computing devices disposed over network 615, possibly including computers remote from the sighted assistant, or even local or remote relative to visually impaired person 605. Additionally, peers 620A can be distributed across one or more nodes of a cloud computing architecture, possibly based on cloud-based systems offered by Google, Salesforce®, Microsoft®, Amazon®, or other services. Each of peers 620A can provide, at least as some level, support for object recognition within captured ambient sensor data. For example one or more object registration module 626 could be distributed among peers 620A where each of peers 620A has different object recognition or registration responsibility as discussed previously. For example, communication paths through peers 620A can be constructed where each peer 620A provides registration information at different image resolutions according a pyramidal encoding/decoding scheme (see FIG. 4). It other embodiments, panoramic engine 620 can represent a single computing device operating as a network-based server offering a service to remote visually impaired people.

Panoramic engine 620 obtains the ambient sensor data from mobile sensing device 610, preferably where the sensor data includes information relating a current field of view (FoV) 630. FoV 630 represents a current collection of data for a portion of remote environment 635. The term "current" is intended to convey the concept that FoV 630 represents a substantially real-time representation of the sensor data, subject to latency. Acceptable latencies considered to fall within the concept of current can be less than one minute, more preferably less than 10 seconds, yet more preferably less than 1 second, or even yet more preferably less than 0.25 seconds.

FoV 630 can be represented by image data (e.g., stills, video, etc.) and position data obtained from the sensors associated with mobile sensing device 610. Panoramic engine 620 converts the image data and position data, possibly including orientation data, into a rendered FoV for presentation to a sighted assistant via assistant interface 650. Furthermore panoramic engine 620 is configured to construct an augmented reality panorama representing a model of remote environment 635, and its associated objects, at least partially based on the ambient sensor data. The augmented reality panorama can also include an integrated current FoV 630. One should appreciate, as discussed previously; panoramic engine 620 can also incorporate other types of ambient data besides visual data into the augmented reality panorama so the augmented reality panorama can comprise multi-modal data.

When panoramic engine 620 collects, or otherwise obtains, ambient data, panoramic engine 620 stitches the data together to create a multi-modal panorama including visual data, audio data, haptic data, kinesthetic data, metadata data or other types of data. Visual data can be stitched together using various suitable techniques include recognizing object features, possible through SIFTs registration, to combine images. One suitable method for constructing panoramas from image data that could be adapted for use with the inventive subject matter includes those described in U.S. Pat. No. 7,424,218 to Baudish et al. titled "Real-Time Preview for Panoramic Images", filed Jul. 28, 2005.

When constructing the augmented reality panorama, panoramic engine 620 can also stitch together different types of data. For example, a basic image of a street might be collected from Google StreetView while objects in the street might be collected from image data received from one or more mobile sensing device 610 utilized by subscribers of the service. Some objects might be permanent (e.g., a lamppost) while other objects might be temporarily (e.g., newspaper machine in lower left corner). Such objects can be superimposed with other data to form the augmented reality panorama. Furthermore, audio data within ambient sensor data can be bound with objects as well. Consider a passing car or truck. Sound from the vehicle can be automatically bound to the image of the vehicle through comparing common attributes or features associated with objects represented by the audio or image data (e.g., position, orientation, size, shape, make, model, etc.).

Panoramic engine 620 is also preferably configured to identify objects within sensor range of remote environment 635. Objects can be identified via different modalities, or combination of modalities, including image data, audio data, wireless data (e.g., Wi-Fi, RFID, etc.) or other types of data. For example, objects in image data can be determined through SIFT features, possibly based on the techniques described in U.S. Pat. No. 7,016,532 to Boncyk et al. titled "Image Capture and Identification System and Process", filed Nov. 5, 2001. Regardless of how objects are identified, panoramic objects can be stored, along with other panoramic parameters in panoramic database 624. Objects can be stored as manageable data objects comprising attributes. Attributes can include object features, names, metadata, time stamps, locations, rendering instructions, or other information.

One should note an augmented reality panorama can include temporal information, or can be considered a dynamic structure. Portions of the panorama can include historical portions representative of historical ambient sensor data. Historical portions can be updated when current ambient sensor data is collected. In view that a panorama has historical content, an astute reader will appreciate that an augmented reality panorama can be time-shifted to freeze or even playback experiences of visually impaired person 605 within remote environment 635 or playback portions of remote environment 635. One can consider the augmented reality panorama as a virtual "black-box" augmented reality of remote environment 635.

Panoramic engine 620 can also filter content within the constructed augmented reality panorama if desired or required. In some scenarios, ambient sensor data can be considered private rather than public. Private data represents data considered to be under management or control of visually impaired person 605, or other authorized individual assuming proper authentication, authorization, or permission levels. In view that the ambient data can include private data; the augmented reality panorama can comprises a personalized panorama associated with visually impaired person 605, or their authorized sighted assistant. If required, the augmented reality panorama can include filtered portions as a function of the private sensor data. For example, when visual impaired person 605 is interacting with a keypad of an ATM machine, panoramic engine 620 can filter, dither, or otherwise obscure visibility of the sighted assistant to the key pad.

Although the augmented reality panorama is constructed for presentation to the sighted assistant via assistant interface 650, the augmented reality panorama can also be considered a shared augmented reality panorama with visually impaired person 605. Panoramic engine 620 can provide object information back to mobile sensing device 610 in the form of device commands instructing mobile sensing device 610 to take appropriate action. Actions can include notifying visually impaired person 605 of proximity to objects (e.g., auditory or haptic feedback), adjust sensor acquisition rates, filter sensor data, or otherwise control remote mobile sensing device 610 from panoramic engine 620 to present augmented reality panorama information. In such a scenario, both the sighted assistant and visually impaired person 605 share the constructed augmented reality panorama. Additional actions can also include instructing mobile sensing device 610 to interact with real-world objects (e.g., vending machines, medical devices, kiosks, printers, etc.).

Figure 7:
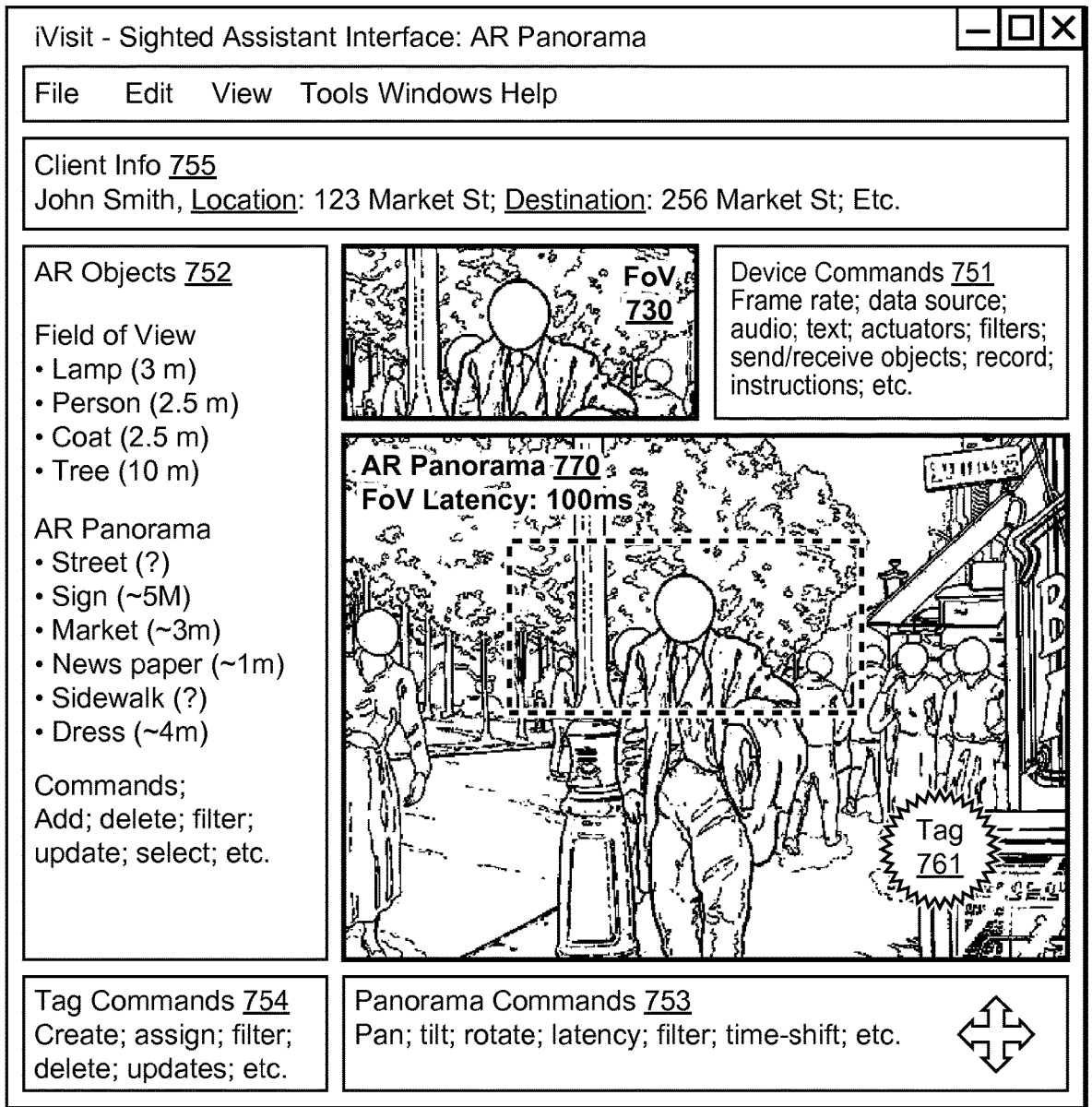
FIG. 7 shows a possible sighted assistant interface configured to present an augmented reality panorama of a remote environment.

Similar to FIG. 3, FIG. 7 presents sighted assistant interface 750 through which a panoramic engine presents constructed augmented reality panorama 770 to a sighted assistant. In the example shown, assistant interface 750 is illustrated as a 2D desktop application possibly executing on a desktop computer. Still, in other embodiments, interface 750 can be presented on mobile device, as a 3D interface via glasses or other appropriate viewing equipment, within a web page, a helmet or chamber providing a 4π steradian view, or other desirable interface. A sighted assistant utilizes assistant interface 750 to provide automatic or manual assistance to the remote visually impaired person.

Although augmented reality panorama 770 is presented as a flat 2D image of the remote environment in which the visually impaired person currently finds himself, one should appreciate augmented reality panorama 770 represents a digital model of the remote environment and includes models of objects within the environment. Objects presented in augmented reality panorama 770 are considered interactive objects allowing the assistant to update object information as desired. Furthermore, as alluded to above, augmented reality panorama 770 can be considered a 3D digital model of the environment, which can also include temporal components. Thus, augmented reality panorama 770 can be considered a 4D model of the remote environment.

Augmented reality panorama 770 represents stitched together information received from one or more ambient data sources. Augmented reality panorama 770 can include both current, updated portions as well as historical portions reflecting previously received ambient sensor data. Preferably augmented reality panorama 770 includes an integrated current FoV 730, possibly superimposed on augmented reality panorama 770 as indicated, where FoV 730 substantially corresponds to the current FoV captured by the mobile sensing device in use by the remote visually impaired person.

As mentioned previously, there can be latency between acquisition of the sensor data from the remote environment and presentation of portions of augmented reality panorama 770. The latency can be presented with one or more portions of the panorama, even at various levels of granularity. In the example, latency is presented for FoV 730. Still, a latency can presented for current portions of augmented reality panorama 770, for historical portions of augmented reality panorama 770, or for objects within augmented reality panorama 770. Providing latency information is considered advantageous because the sighted assistant can gain an understanding of how stale or up-to-date portions of the model actually are, which can be useful when aiding the visually impaired person in the remote environment.

The sighted assistant can interact with augmented reality panorama 770 as desired, possibly through one or more panorama commands 753. In view that augmented reality panorama 770 represents a more complex model of the remote environment and its objects than just an image; the assistant can navigate around the augmented reality panorama 770 separately from the visually impaired person. For example, the assistant could zoom into the augmented reality panorama 770 to walk figuratively ahead of the visually impaired person, assuming augmented reality panorama 770 includes portions based on additional sensor data, to determine if the way is clear of obstacles. Other panorama commands 753 can include pan, tile, rotate, filter, time shift, or otherwise adjust the presentation of the augmented reality panorama 770.

Augmented reality panorama 770 includes one or more of augmented reality objects 752, possibly presented in a list format as shown. Augmented reality objects 752 can be segregated as desired, possibly by those objects within FoV 730 and objects outside FoV 730. Separating objects according to such a scheme is considered advantageous because the organization provides the sighted assistant insight into which objects in augmented reality panorama 770 are likely to be more temporally relevant than others. Augmented reality objects 752 outside of FoV 730 (e.g., the news paper vending machine) might be stale based on old data.

Augmented reality panorama 770 can also present additional information related to augmented reality objects 752. Each of augmented reality objects 752 can also be presented with associated attributes or metadata as desired. For example, tag 761 is illustrated euphemistically to represent attributes or metadata assigned to an object. The object information can be presented according to many different schemes as desired. Example object information includes object names, object locations, time-stamps of object updates, relevant features or object landmarks (e.g., SIFT registration, edges, corners, etc.), metadata assignments, object dimensions, colors, or other types of information that can be bound to augmented reality objects 752.

The panoramic engine responsible for creating augmented reality panorama 770 can also auto populate augmented reality panorama 770 with augmented reality objects 752 and auto populate their object attributes. As augmented reality objects 752 are recognized by their features (e.g., SIFT registration landmarks, locations, colors, etc.), the engine can bind the attributes to the object. In the example shown, one type of attribute that is auto populated includes relative distances from the origin of FoV 730 to the various objects. Depending on how recently the panoramic engine collected ambient sensor data, some distances might be more accurate than others. For example, augmented reality objects 752 in FoV 730 would likely have more accurate distances if they are dynamically moving objects due to the low latency of the collected data, while objects outside FoV 730 might have associated stale data, which likely results in less accurate distance estimations.

One should keep in mind that a human sighted assistant can also manually manage augmented reality objects 752. For example, assistant interface 750 can also present a human sighted assistant with one or more object commands allowing the assistant to manage augmented reality objects 752. Contemplated object commands can include add, delete, assign metadata, update, select, filter, save, or otherwise manage the objects. Consider a scenario where the lamppost has not yet been identified or has not been auto populated within augmented reality panorama 770. The sighted assistant could trace an outline of the lamppost using a mouse pointer and instruct the panoramic engine to create or add the lamppost as an object. The assistant can further assign one or more metatags to the object as desired, or the panoramic engine can also assign metatags to the objects (e.g., locations, color, shape, etc.) based on correlating the input from the assistant with features or registration landmarks of the defined object. Another scenario can include the sighted assistant placing virtual way point objects within augmented reality panorama 770 which can then be sent to the device of the visually impaired person. The person can use audio or haptic feedback (i.e., device commands) from the way point objects to navigate the corresponding real-world.

FoV 730 can be integrated within augmented reality panorama 770 as a function of the mobile sensing device position information received within ambient sensor data. In more preferred embodiments, the panoramic engine superimposes FoV 730 on augmented reality panorama 770 to ensure the sighted assistant gains an understanding of where the remote mobile sensing device is currently positioned relative to augmented reality objects 752 within augmented reality panorama 770. The position and orientation of FoV 730 can be determined from corresponding data received in the ambient sensor data. In some embodiments, the position data can include GPS coordinates, and orientation data can be obtained from accelerometer data or magnetometer data. The placement of FoV 730 can be refined by combining multiple modalities of data to correct, adjust, or refine its position. Combining two or more modalities is considered to offer a more accurate placement. For example, object features (e.g., object landmarks, SIFT registration landmarks, etc.) can be combined with GPS data to correct a location of FoV 730 by triangulation relative to the object landmarks. Furthermore, audio data, possibly including amplitude, frequency, or phase information (e.g., echo location, Doppler, etc.), can be combined with image data or even accelerometer data to determine location of objects or FoV 730. Accelerometer data can be integrated once to determine velocity or twice to determine distance covered, then combined with GPS information or other data types to reduce errors in determining locations or orientation. In short, placement of FoV 730 can be corrected based on at least two sensor data types. Sensor data types can include GPS location, image registration data, accelerometer data, magnetometer data, wireless data (e.g., Wi-Fi positioning, RFID data, wireless triangulation, etc.), odometry data, audio data (e.g., sounds, echo location, etc.), or other types of data. One should note that as the sighted assistant navigates through augmented reality panorama 770, FoV 730 can retain its proper position or orientation with respect to augmented reality panorama 770 even if the assistance rotates their view. Thus, is it contemplated that assistant interface 750 can also present FoV 730 separately as illustrated.

Augmented reality objects 752 can be highlighted within augmented reality panorama 770 as euphuistically represented by superimposed tag 761. Highlighting augmented reality objects 752 can be achieved through various methods. In some embodiments, objects comprise highlighted outlines, icons, or other indicators illustrating that augmented reality objects 752 are present in augmented reality panorama 770. An especially preferred indicator comprises a highlight indicating differences between historical portions of augmented reality panorama 770 and recently updated portions of augmented reality panorama 770. Such an approach is useful when the remote visually impaired person enters a dynamic environment where augmented reality objects 752 might shift or change. For example, the news paper vending machine in the lower right corner might be newly placed on the street as indicated by the presence of tag 761.

As mentioned briefly above, the sighted assistant can also assign metatags, tag 761 for example, as metadata to augmented reality objects 752 within augmented reality panorama 770 via tag commands 754. The tags can include a visual tag or a non-visual tag. A visible tag can be represented as an icon or other indicator visible to the sighted assistant and can provide a listing of properties of the object. One should also appreciate that non-visual tags can include auditory or even haptic metadata, which can be used to identify the object to the remote visually impaired person. Contemplated tag commands can comprise many different tag management actions including creating, deleting, modifying, moving, saving, filtering, or otherwise managing object tags. Assigning metatags to objects provides a great deal of flexibility toward personalizing the augmented reality panorama 770 to a specific client.

As sighted assistant or the visually impaired person interact with shared augmented reality panorama 770, augmented reality objects 752 can be dynamically updated as discussed above. One should recall the many augmented reality objects 752 can be considered public objects, which can be incorporated into other augmented reality panoramas from other clients or subscribers to the service. Thus, augmented reality panorama 770 or its augmented reality objects 752, can be shared among multiple users, subject to privacy concerns. Furthermore, augmented reality panorama 770 can also be considered to include Wiki portions reflecting shared or publicly available or updatable aspects of augmented reality panorama 770. Example Wiki-like portions can include annotations, objects, revisions, or other user-submitted augmented reality content.

For illustrative purposes augmented reality panorama 770 presents portions that have been filtered as indicated by blank faces the people in the augmented reality panorama 770 where, at least for this example, face data is considered private data. Even if private image data is acquired, the panoramic engine can recognize features of the private data (e.g., faces, security items, etc.) and remove, or otherwise obscure the private data for privacy concerns. Augmented reality panorama 770 can include other types of filtered portions as desired or as configured. Example uses of filtered portions can include obscuring a home environment, obscuring specific individuals, obscuring security inputs, or obscuring other items considered private. Obfuscation can also be applied to other types of data including audio data, location data, destinations, rate of movement, or other information. The panoramic engine can correlate object features (e.g., SIFT registrations, audio signatures, etc.) with objects. When the features satisfy filtering criteria, the objects can be obscured within augmented reality panorama.

The sighted assistant has numerous options available to aid the remote visually impaired person. One option simply includes establishing a voice communication link via the smart phone with the person. The sighted assistance can discuss the person's current circumstances and provide verbal assistance. More preferred approaches include using the assistant interface 750 to transmit one or more device commands 751 to the remote mobile sensing device to control operation of the device. The device commands 751 can comprise a wide range of instructions that direct the mobile sensing device to capture additional object information associated with the augmented reality objects 752 or yet to be identified objects within augmented reality panorama 770.

Device commands 751 can take on many different forms depending on the requirements or desires of the assistant. Example commands can include changing data acquisition frame rate for video, adjusting resolution of capture images, change sampling rate for audio capture, adjusting compression or encryption parameters of exchanged data, alternating communication paths between the remote sensing device and the panoramic engine, instructing device to trigger on or more actuators (e.g., weighted plungers, vibrators, Braille pads, etc.), emit audible signals representing object proximity, or other control commands. Thus, the sighted assistant can control the remote sensing device to enhance augmented reality panorama 770 as well as assist the remote visually impaired person. Consider a scenario where the visually impaired person wishes to purchase a new paper. The sighted assistant can issue device commands 751 to the device causing the device to vibrate or emit sounds as the visually impaired person nears the new paper vending machine.

As discussed with respect to FIG. 1, aspects of the object recognition technology can be deployed within the remote sensing device or an add-on adapter. In view that a device-base recognition application can be resident proximal to or even within the device, the device commands 751 can also include high level instructions directed toward the recognition application to control or manage the application's operation. For example, the assistant can instruct the device to toggle operation of one or more recognition algorithms that are more suited to capturing additional information about the remote environment or objects in the remote environment. One algorithm might be better suited for OCR rather than face recognition or object recognition. Consider a scenario where the remote visually impaired person is working with money. The sighted assistant can instruct the remote device to employ recognition algorithms tailored to identifying currency, possibly based on geographic location (e.g., country) rather than a generic object recognition algorithm requiring additional processor power. Such an approach provides for optimized interactions with real-world objects where selected algorithms can be employed more efficiently than others for current circumstances.

Although the above discussion references an assistant as a human operator, one should appreciate that the panoramic engine or even portions of assistant interface 750 can also operate as an automated sighted assistant. Many interactions between the remote visually impaired person and augmented reality panorama 770 can be automated. As discussed previously, assistant interface 750 when operated in an automated fashion can send feedback to the visually impaired person indicating relative distances to known or discovered objects within augmented reality panorama 770. In such embodiments, assistant interface 750 can operate as a module within a panoramic engine where the module operates as an expert system offering recommendations back to the visually impaired person via one or more application program interfaces. Furthermore, the visually impaired person or a human sighted assistant can programmatically configure automated responses or actions based on movement of the visually impaired person through the real-world, which trigger actions based on criteria dependent on object features (e.g., SIFT registrations, audio signatures, textures, etc.) within augmented reality panorama 770.

Thus, the present application discloses systems and methods directed to providing flexible, powerful, and user responsive solutions configured to accurately and conveniently provide object, facial, context, or environmental recognition as part of an integrated approach to augmenting sight, especially within a shared augmented reality panorama. Among the many benefits disclosed by the present application are devices, systems, and methods for providing a mobile user with real-time sighted assistance, information, or communication through accessible interfaces. For example, augmented reality or enhanced sight services can be provided using a camera-enabled, or sensor-enabled, portable communication device connected to a user's personal computer (PC) and/or other centralized or distributed computing and communication services.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A computer implemented method of generating a visual representation of collected sensor data, the method comprising:
   receiving sensor data from a plurality of remote devices over a network, the sensor data including at least image data and associated location data, the plurality of remote devices each being a mobile device;
   storing the sensor data in a database, the sensor data addressable by at least the associated location data;
   collecting sensor data from the database based on a target mobile device location obtained from a target mobile device and the associated location data from at least one of the plurality of remote devices;
   using at least one processor, constructing a visual representation associated with the target mobile device location based on the collected sensor data and on a camera field of view of at least one of the plurality of remote devices, wherein said constructing the visual representation includes combining the sensor data according to the location data of the plurality of remote devices; and
   displaying the visual representation on a device and causing the device to enable commands within the visual representation.

2. The method of claim 1, further comprising coupling with a peer-to-peer network operating as the network.

3. The method of claim 1, further comprising coupling with at least one of the following types of remote devices over the network: a mobile device, a portable device, a smart phone, and glasses.

4. The method of claim 1, wherein the sensor data further includes at least one of the following data modalities: video data, video stream data, audio data, accelerometer data, magnetic data, bio data, barcode data, RFID data, odometer data, and health metric data.

5. The method of claim 1, wherein the sensor data comprises ambient sensor data from the plurality of remote devices.

6. The method of claim 1, wherein the visual representation comprises a 2D map.

7. The method of claim 1, wherein the visual representation comprises a 3D map.

8. The method of claim 1, further comprising storing recognizable objects based on the sensor data.

9. The method of claim 1, wherein the visual representation comprises a panorama.

10. The method of claim 9, wherein the panorama comprises at least a two dimensional augmented reality panorama.

11. The method of claim 10, wherein the panorama comprises at least a three dimensional augmented reality panorama.

12. The method of claim 9, wherein the visual representation comprises a live panorama.

13. The method of claim 9, wherein the commands include panorama commands.

14. The method of claim 1, wherein the commands include at least one of the following: pan, tilt, rotate, filter, and time shift.

15. The method of claim 1, wherein the field of view comprises a real-time field of view.

16. The method of claim 1, wherein the visual representation comprises multi-modal data.

17. The method of claim 16, wherein the multi-modal data comprises at least one of the following data modalities: visual data, audio data, haptic data, kinesthetic data, and metadata data.

18. The method of claim 1, wherein the sensor data comprises registration features including at least one of the following: SIFT features, SURF features, environment features, landmark features, text features, audio features, and barcode features.

19. The method of claim 1, wherein the visual representation comprises network links to information related to objects.

20. The method of claim 19, wherein the network links initiate location based services based on the location data.

21. The method of claim 1, wherein the location data comprises global positioning system data.

22. The method of claim 1, wherein the location data comprises image features.

23. The method of claim 1, further comprising storing recognizable objects in a recognition database.

24. The method of claim 23, wherein the recognition database comprises a private database.

25. The method of claim 24, wherein the visual representation comprises a personalized visual representation constructed from the private database.

26. The method of claim 23, wherein the recognition database comprises a shared community database.

27. The method of claim 26, wherein the visual representation comprises a shared visual representation.

28. The method of claim 1, wherein the commands include device commands.

29. The method of claim 28, wherein the device commands include at least one of the following: change data acquisition rate, change sampling rate, adjust resolution, adjust compression parameters, adjust encryption parameters, alternate communication path, trigger an actuator, emit audible signals, and manage an application.

30. The method of claim 1, wherein the commands include object management commands related to objects.

31. The method of claim 30, wherein the object management commands include at least one of the following: add, delete, assign metadata, tag, update, select, filter, and save.

32. The method of claim 1, wherein the plurality of remote devices include remote devices having different location data.

33. The method of claim 1, wherein the plurality of remote devices includes the target mobile device.

34. A non-transitory computer readable storage medium storing instructions executable by at least one processor to perform operations for generating a visual representation of collected sensor data, the operations comprising:

receiving sensor data from a plurality of remote devices over a network, the sensor data including at least image data and associated location data, the plurality of remote devices each being a mobile device;

storing the sensor data in a database, the sensor data addressable by at least the associated location data;

collecting sensor data from the database based on a target mobile device location obtained from a target mobile device and the associated location data from at least one of the plurality of remote devices;

constructing a visual representation associated with the target mobile device location based on the collected sensor data and on a camera field of view of at least one of the plurality of remote devices, wherein said constructing the visual representation includes combining the sensor data according to the location data of the plurality of remote devices; and displaying the visual representation on a device and causing the device to enable commands within the visual representation.

35. A system for generating a visual representation of collected sensor data, the system comprising:

a plurality of mobile devices, the plurality of mobile devices including a target mobile device and at least one additional remote device; and a server for receiving sensor data including at least image data and associated location data from the at least one additional remote device over a network, storing the sensor data in a database to be addressable by at least the associated location data, collecting sensor data from the database based on a target mobile device location of the target mobile device and the associated location data from the at least one additional remote device, constructing a visual representation associated with the target mobile device location based on the collected sensor data and on a camera field of view of the at least one additional remote device, and displaying the visual representation on a device and causing the device to enable commands within the visual representation, wherein said constructing the visual representation includes combining the sensor data according to the location data of the at least one additional remote device.

* * * * *